(12) United States Patent
Olivares Velasco

(10) Patent No.: US 10,172,406 B2
(45) Date of Patent: *Jan. 8, 2019

(54) DATA COLLECTING HEAD GUARD SYSTEMS AND METHODS THEREOF

(71) Applicant: 2nd SKULL, Inc., Cranberry Township, PA (US)

(72) Inventor: Federico Olivares Velasco, Cranberry Township, PA (US)

(73) Assignee: 2nd Skull, Inc., Pittsburgh, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/693,542

(22) Filed: Sep. 1, 2017

(65) Prior Publication Data
US 2018/0007990 A1 Jan. 11, 2018

Related U.S. Application Data

(63) Continuation of application No. 15/097,942, filed on Apr. 13, 2016, now Pat. No. 9,775,396.

(60) Provisional application No. 62/147,309, filed on Apr. 14, 2015.

(51) Int. Cl.
| | | |
|---|---|---|
| *A42B 3/04* | (2006.01) |
| *H04B 1/3827* | (2015.01) |
| *H04L 29/08* | (2006.01) |
| *H04Q 9/00* | (2006.01) |
| *G08B 21/04* | (2006.01) |
| *A42B 3/12* | (2006.01) |
| *A63B 24/00* | (2006.01) |
| *A61B 5/00* | (2006.01) |
| *G08B 13/196* | (2006.01) |
| *A61B 5/024* | (2006.01) |
| *A61B 5/0402* | (2006.01) |

(Continued)

(52) U.S. Cl.
CPC .............. *A42B 3/046* (2013.01); *A42B 3/125* (2013.01); *A61B 5/0022* (2013.01); *A61B 5/6803* (2013.01); *A61B 5/6804* (2013.01); *A63B 24/0062* (2013.01); *G08B 13/19621* (2013.01); *G08B 21/0438* (2013.01); *H04B 1/3833* (2013.01); *H04L 67/12* (2013.01); *H04Q 9/00* (2013.01); *A61B 5/02438* (2013.01); *A61B 5/0402* (2013.01); *A61B 5/0816* (2013.01); *A61B 5/14517* (2013.01); *A61B 5/4266* (2013.01); *A63B 2220/31* (2013.01); *A63B 2220/53* (2013.01); *H04Q 2209/40* (2013.01); *H04Q 2209/43* (2013.01); *H04Q 2209/50* (2013.01)

(58) Field of Classification Search
None
See application file for complete search history.

(56) References Cited

U.S. PATENT DOCUMENTS

| | | | |
|---|---|---|---|
| 2011/0181420 A1* | 7/2011 | Mack ..................... | A42B 3/046 340/573.1 |
| 2011/0219852 A1* | 9/2011 | Kasten ..................... | A61B 5/11 73/12.04 |

(Continued)

*Primary Examiner* — Thomas McCormack
(74) *Attorney, Agent, or Firm* — Ulmer & Berne LLP

(57) ABSTRACT

A head guard is provided. The head guard includes one or more sensors as part of an sensory input and communications system. The head guard wirelessly communicates data to remote computing devices for intelligent data collection.

20 Claims, 27 Drawing Sheets

(51) Int. Cl.
*A61B 5/08* (2006.01)
*A61B 5/145* (2006.01)

(56) References Cited

U.S. PATENT DOCUMENTS

2014/0006045 A1* 1/2014 Wund, II ............ G06F 19/3487
 705/2
2015/0135412 A1* 5/2015 Shefner .................... A42B 1/08
 2/413

* cited by examiner

DATA COLLECTING HEAD GUARD SYSTEMS AND METHODS THEREOF

CROSS REFERENCE TO RELATED APPLICATION

This application is a continuation of U.S. Ser. No. 15/097,942, filed on Apr. 13, 2016, which claims the benefit of U.S. provisional patent application Ser. No. 62/147,309, filed on Apr. 14, 2015, the disclosure of which are incorporated herein by reference in their entirety.

TECHNICAL FIELD

The systems and methods described below relate generally to the field of head protection. More particularly, the systems and methods relate to head guards that can be worn during sporting, or athletic, or other physical endeavors that can electronically collect input data from one or more onboard sensors and communicate the data to one or more recipient computing devices.

BACKGROUND

When an individual participates in contact sports activities such as football, lacrosse, hockey, soccer, rugby, basketball, volleyball and the like, or other physical activities, such as skiing, skateboarding, and the like, it is common that parts of the individual's body are subject to impact and other physical contact. Various attempts have been made to provide padding as a means of protecting the individual during such activities. Conventional protective equipment can include, as nonlimiting examples, helmets, shoulder pads, thigh pads, and shin pads. Typical protective equipment may include reinforced-sponge type padding, such as a rubber sponge layer laminated with a stiff plastic layer.

BRIEF DESCRIPTION OF THE DRAWINGS

The present disclosure will be more readily understood from a detailed description of some example embodiments taken in conjunction with the following figures:

FIGS. 30-34A show example winter hats that incorporate a head guard.

DETAILED DESCRIPTION

Figure 3:
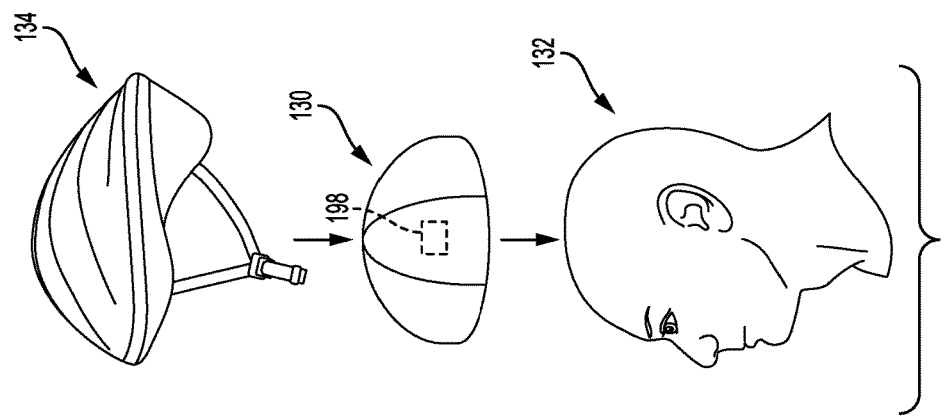
FIGS. 1-3 show example head guards used in combination with example helmets.

Various non-limiting embodiments of the present disclosure will now be described to provide an overall understanding of the principles of the structure, function, and use of head guards having onboard sensors and componentry for data collection and transmission disclosed herein. One or more examples of these non-limiting embodiments are illustrated in the accompanying drawings. Those of ordinary skill in the art will understand that systems and methods specifically described herein and illustrated in the accompanying drawings are non-limiting embodiments. The features illustrated or described in connection with one non-limiting embodiment may be combined with the features of other non-limiting embodiments. Such modifications and variations are intended to be included within the scope of the present disclosure.

The presently disclosed embodiments are generally directed to head guard, head guard systems, methods of using a head guard, and methods of manufacturing head guards. Head guards in accordance with the present disclosure can have one or more onboard data collection devices (referred to herein as sensors) that can collect, sense, record, or otherwise gather various information, events, environmental data, and/or operational data. Such systems and methods may be implemented in a wide variety of contexts and applications. In one example embodiment, the head guard is compressive so that it can be retained on a user's head without the use of a securing strap, such as a chinstrap. The head guards can be constructed with one or more layers, sections, or pockets of impact absorbing or impact dissipating materials, referred to generally herein as padding. The particular type of padding can vary based on a variety of factors, such as style of head guard, sporting or athletic application, type of user, size of head guard, and so forth. As described in more detail below, in some embodiments, the head guard can have three layers, including an inner layer, a middle layer, and an outer layer. The middle layer can comprise the padding. Other embodiments of head guards can have more than three layers or less than three layers. The head guard can comprise, for example, one or more thermal layers or at least portions of thermal protection (e.g., around the ears). Such embodiments can be useful for wearers participating in cold-weather endeavors. In some example embodiments, the head guard can be washable without necessarily removing the padding layer from the head guard. The head guard can also have breathable characteristics, water repellent characteristics, sweat wicking characteristics, or other comfort related characteristics, such as vents. The head guard can have water resistant or water repellant qualities. In some embodiments, the head guard can include an anti-bacterial agent, anti-microbial agent, anti-odor agent, or other deodorizing or sanitizing compounds. In some embodiments, the head guard is configured to provide protection against ultraviolet rays using any suitable techniques, such as chemical treatments, construction techniques, materials, and so forth. As described in more detail below, the head guard can be sized for a child wearer or an adult wearer. One or more sensors can be integrated into the head guard. In some embodiments, various sensors can be permanently affixed or otherwise embedded to a head guard. In other embodiments, various sensors (or portions thereof) are removable. In some embodiments, various sensors are interchangeable or swappable. The one or more sensors of a head guard can communicate with an onboard microcontroller through any suitable communications network onboard the head guard.

In some embodiments, textile integrated sensors, sometimes referred to as bio sensing fabrics, can be utilized. Generally, textile integrated sensors can measure a large variety of variables, e.g. physical dimensions like pressure, stress and strain applied to the textile or biomedical dimensions such as heart rate, electrocardiogram (ECG), sweat rate and sweat composition (salts, pH), respiration rate of a wearer of the head guard. In some embodiments, sensor(s), electrode(s) and connections can be fully integrated in the fabric of the head guard and produced by combining conductive and non-conductive yarns.

In some embodiments, a head guard can include various types of communication capabilities, such as wireless communication abilities. In some embodiments, a head guard can communicate on a personal area network (PAN) such as using a BLUETOOTH protocol, or other suitable near field communication (NFC) protocols, to a linked electronic device. Using this communication functionally, a head guard can provide information gathered by one or more of the sensors to a linked electronic device. Such information can be provided in real-time, substantially real-time, in batch format, or other suitable periods or timetables. Various types of electronic devices can be linked, such as mobile phones, tablets, laptop computers, desktop computers, wearables, and the like. In some embodiments, as described in more detail below, the linked electronic device can executed a specialized application that is configured to collect data and provide various visualizations, alerts, information, data, and/or other analytics to a user based on data received from an associated head guard. In some embodiments, one or more of the linked electronic devices can also be in communication with a centralized activity monitoring computing system (such as a cloud-based service) that can collect and aggregate data from a plurality of head guards.

In some embodiments, as described in more detail below, the head guard may be worn underneath a wide variety of helmets, such as football helmets, batting helmets, bicycle helmets, and so forth. In some embodiments, the head guard may be incorporated into, formed with, or otherwise coupled to various head coverings, such as a baseball hat, a winter hat, a hood on a sweatshirt or jacket, or other styles of hat. In some embodiments, the head guard can be incorporated into apparel (hats, hoods, and so forth) in a discrete fashion, such that it is not necessarily apparent from an observer that the apparel includes the head guard. In some embodiments, a head guard can be the only piece of protective gear on the wearer's head. As described in more detail below, the head guard can be configured to cover various parts of the wearer's head, such as the crown, or be of a headband configuration that surrounds the wearer's head.

In some embodiments, as described in more detail below, the head guard may be worn over top of a wide variety of helmets, such as football helmets, batting helmets, skateboarding helmets, snowboarding helmets, and so forth.

As is to be appreciated, the head guard described herein can be sized to accommodate different ages of users. In one example embodiment, a child's "one size fits all" head guard is sized to fit children and an adult's "one size fits all" head guard is sized to fit adults. As described in more detail below, elastic components incorporated into the head guard can aid in maintaining the head guard on a user's head while also allowing the head guard to accommodate different sized heads. In some embodiments, head guards can be manufactured in different sizes (small, medium, large, x-large, and so forth). In some embodiments, the head guard may be selectively adjustable to accommodate different head sizes.

Reference throughout the specification to "various embodiments," "some embodiments," "one embodiment," "some example embodiments," "one example embodiment," or "an embodiment" means that a particular feature, structure, or characteristic described in connection with the embodiment is included in at least one embodiment. Thus, appearances of the phrases "in various embodiments," "in some embodiments," "in one embodiment," "some example embodiments," "one example embodiment, or "in an embodiment" in places throughout the specification are not necessarily all referring to the same embodiment. Furthermore, the particular features, structures or characteristics may be combined in any suitable manner in one or more embodiments.

Throughout this disclosure, references to components or modules generally refer to items that logically can be grouped together to perform a function or group of related functions. Like reference numerals are generally intended to refer to the same or similar components. Components and modules can be implemented in software, hardware, or a combination of software and hardware. The term "software" is used expansively to include not only executable code, for example machine-executable or machine-interpretable instructions, but also data structures, data stores and computing instructions stored in any suitable electronic format, including firmware, and embedded software. The terms "information" and "data" are used expansively and includes a wide variety of electronic information, including executable code; content such as text, video data, and audio data, among others; and various codes or flags. The terms "information," "data," and "content" are sometimes used interchangeably when permitted by context. It should be noted that although for clarity and to aid in understanding some examples discussed herein might describe specific features or functions as part of a specific component or module, or as occurring at a specific layer of a computing device (for example, a hardware layer, operating system layer, or application layer), those features or functions may be implemented as part of a different component or module or operated at a different layer of a communication protocol stack. Those of ordinary skill in the art will recognize that the systems, apparatuses, devices, and methods described herein can be applied to, or easily modified for use with, other types of equipment, can use other arrangements of computing systems such as client-server distributed systems, and can use other protocols, or operate at other layers in communication protocol stacks, than are described.

Figure 2:
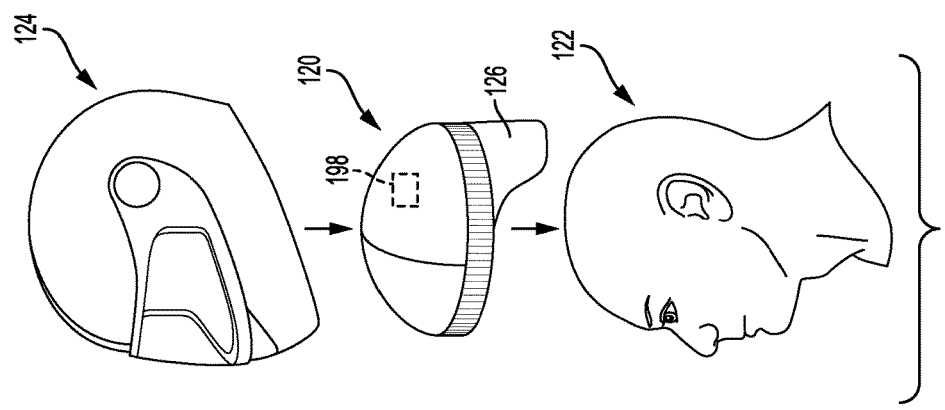
Figure 1:
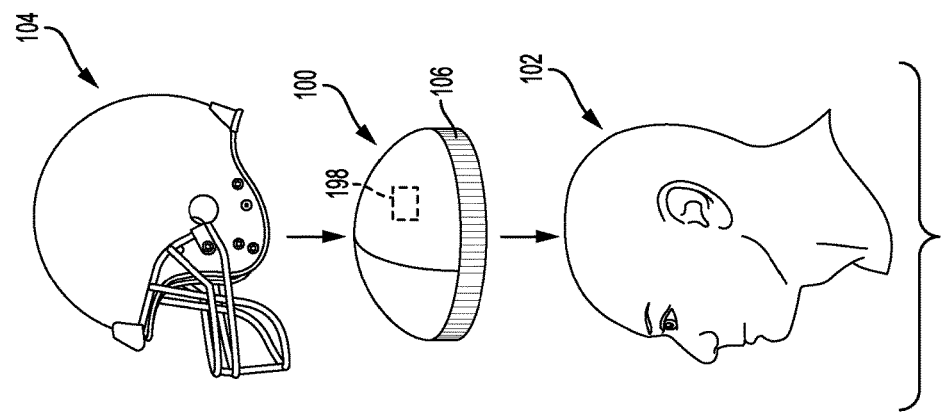

Referring now to FIGS. 1-3, example embodiments of the present disclosure show head guards are used in combination with various example helmets. Each of the head guards schematically depicts a sensory input and communications system 198. The sensory input and communications system 198 can include any suitable number of sensors, each sensor being of any suitable type. As used herein, the term sensor is to broadly include any component or device configured to provide a particular output based on an input. In this regard, example sensors can include, without limitation accelerometers (for speed, linear impact), movement sensors, superconducting quantum interference device ("SQUID") sensors, magnetometers (for rotational impact), gyroscope (for angular velocity), temperature sensors (for ambient and/or body temperature), acoustic sensors, chemical sensors, density sensors, positional sensors, fluid sensors, proximity sensors, humidity sensors, vibration sensors, radiation sensors, navigation sensors, barometric sensors, image sensor (e.g., video image, static image, brain imaging, etc.). The output(s) can be provided to a microcontroller of the sensory input and communications system 198. The sensory input and communications system 198 can also include various wireless communication componentry to transmit various data to a receiving computing unit. Additional detail regarding example sensory input and communications system is discussed below with regard to FIGS. 42-47

Referring first to FIG. 1, a head guard 100 is positionable upon a head 102 of a user. As described in more detail below, the head guard 100 can include a plurality of layers which includes a padding layer. The head guard 100 can be generally compressive such that its position on the head 102 can be maintained without the use of chin strap. Other embodiments, however, can use additional fastening features. The head guard 100 in FIG. 1 comprises an elastic member 106 which aids in securing the head guard 100 to the head 102. The elastic member 106 may encircle the entire head guard (as shown) or may be limited to certain portions of the head guard, such as the front and/or rear. The elastic member 106 can comprise, for example, an elastic band or cord positioned in a hem. Subsequent to placing the head guard 100 on the head 102, a helmet 104 can be placed onto the head 102 and over top of the head guard 100. The head guard 100 can be relatively thin as compared to the helmet 104 such that the head guard 100 does not interfere with the usability and comfort offered by the helmet 104. As illustrated, helmet 104 is a football helmet. It is noted that the present disclosure is not limited to football helmets. Instead, a wide array of different helmets can be used in in combination with the head guard 100, such as helmets worn by pilots, firemen, construction workers, or by any other person wearing any type of helmet or head protection. FIG. 2, for example, illustrates a motocross helmet 124 for a head 122 of a user. A head guard 120 can be positioned over the head 122 and under the motocross helmet 124. In the illustrated embodiment, the head guard 120 comprises a neck panel 126. As is to be appreciated, any suitable configuration of head guard can be used with any suitable helmet. Similar to the head guard 100, the head guard 120 also comprises an elastic member 126 which generally aids in retaining the head guard 120 on the head 122 of the user. In some embodiments, drawstrings, buckles, or other tightening features may be used.

As is to be appreciated, the particular configuration of the head guard can be based on, for example, the type of helmet to be worn with the head guard and/or the type of activity to be performed while wearing the head guard. FIG. 3, for example, illustrates an example head guard 130 for use with a bicycle helmet 134. The head guard 130 can be placed on a head 132 of the user prior to securing the bicycle helmet 134 to the head 132. In the illustrated embodiment, the compressive nature of the head guard 130 generally maintains the placement of the head guard 130 on the head 132 without the use of an additional elastic feature. While a football helmet, motocross helmet, and bicycle helmet are illustrated in FIGS. 1-3, the present disclosure is not limited to these particular application types. Instead, the head guards described herein can be used in combination with any suitable helmet type or form of head protection.

Figure 4:
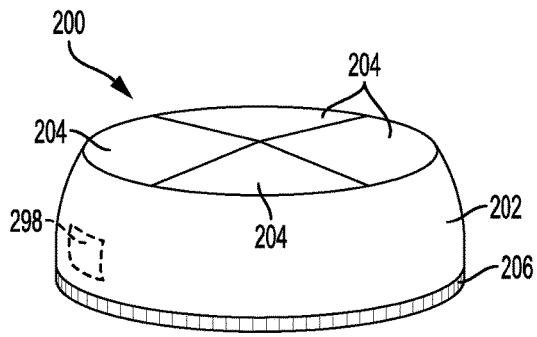
FIGS. 4-16C are perspective views of example head guards.

FIGS. 4-16 illustrate non-limiting examples of head guard configurations. As is to be appreciated, features of head guards of some embodiments can be incorporated into the head guards of other embodiments without departing from the scope of this disclosure. Each of the head guards in FIGS. 4-16 is schematically shown to include a sensory input and communications system 298. Head guard 200 in FIG. 4, for example, is comprised of a circumferential panel 202, sometimes referred to as a sidewall, and a plurality of top panels 204. The top panels 204 can be generally triangular such that, when they are coupled to each other, they generally form a disc. As described in more detail below, various types of padding can be incorporated into one or more of circumferential panel 202 and one, more than one, or none of the top panels 204. While FIG. 4 shows an elastic member 206 coupled to the circumferential panel 202, other embodiments may use other types of retention features. For example, elastic characteristics of the circumferential panel 202 may be used to maintain the head guard 200 on the head of a user. As with other head guards described herein, the size of the head guard 200 can be designed such that it is appropriate for the particular type of user (child, teenage, adult, and so forth).

Figure 5:
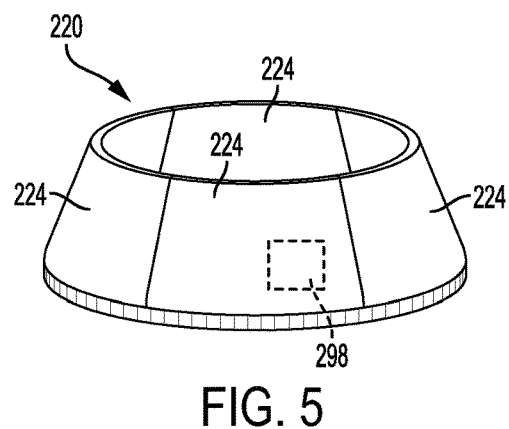
Figure 6:
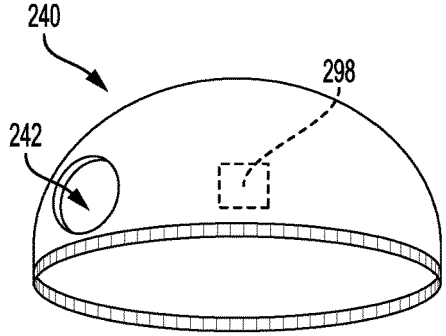
Figure 7:
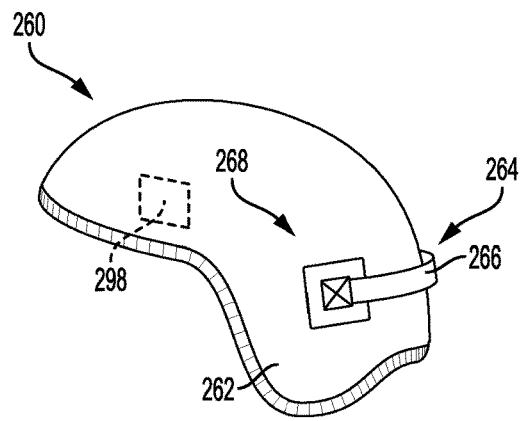
Figure 8:
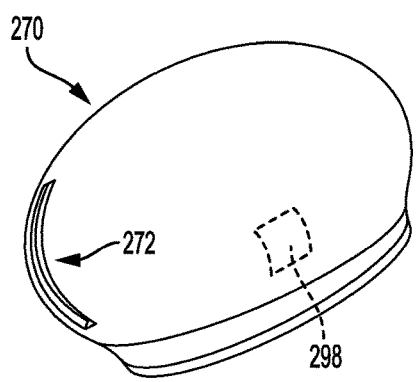

Head guard 220 illustrated in FIG. 5 shows an embodiment that does not cover the top of a user's head. Instead, the top of the head guard 220 is open (e.g., a band-like configuration). The head guard 220 can be used, for example, for non-contacting sports. For instance, it can be worn by a soccer player who may frequently use the top of their head to contact the soccer ball. Other examples of non-contacting sports can include, without limitation, basketball, running, volleyball, or any other sport or endeavor that does not necessarily utilize a rigid helmet. While the head guard 220 is shown constructed of a plurality of panels 224, other constructions techniques may be utilized without departing from the scope of the present disclosure. FIG. 6 shows yet another embodiment of a head guard 240 in accordance with the present disclosure. The head guard 240 shown in FIG. 6 includes a rear aperture 242. A wearer of the head guard 240 that has a pony tail can pull the pony tail through the rear aperture 242. The aperture 242 can have any suitable dimension or configuration. In one embodiment, the aperture 242 has a diameter in the range of about 1" to about 3". While the aperture 242 is illustrated as being circular, it is to be appreciated that any suitable shape can be used, such as rectangular, oblong, triangular, and so forth. Referring now to FIG. 7, a head guard 260 is shown having temple guards 262. The head guard 260 also has a tightening feature 264. In the illustrated embodiment, the tightening feature 264 is a strap 266 that is fixed to the head guard at a fixed end and comprises a hook-and-loop fastener assembly 268 at the other end. A user can selectively attach and detach the hook-and-loop fastener assembly 268 to select an appropriate fit for the head guard 260. FIG. 8 shows yet another embodiment of a head guard 270 in accordance with the present disclosure. The head guard 270 shown in FIG. 8 includes a rear aperture 272. A wearer of the head guard 270 that has a pony tail can pull the pony tail through the rear aperture 242. The aperture 272 shown in FIG. 8 is a slot or slit in a vertical orientation. In other embodiments, the aperture 272 can be a slot or slit in a horizontal orientation, an oblique orientation, or a plurality of slots or slits arranged in a suitable formation, for example.

Figure 9:
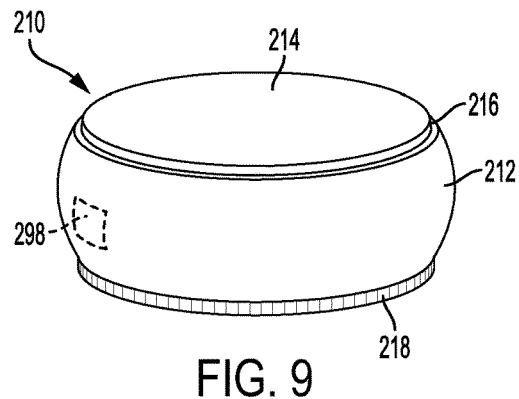

The head guard 210 shown in FIG. 9 comprises a sidewall 212 and a top panel 214. The sidewall 212 can be a multi-layered sidewall comprising at least one fabric layer and at least one padding layer, as described in more detail below. The top panel 214 can also comprises at least one fabric layer and at least padding layer. In the illustrated embodiment, the top panel 214 is attached to the sidewall 212 using stitching 216, although any suitable attachment technique can be used, such as a gluing, heat welding, and so forth. The head guard 210 also comprises an elastic portion 218 that is positioned proximate to an opening defined by the sidewall 212. The head guard 210 can be in a generally cylindrical shape when in a relaxed configuration (as shown). When the head guard 210 is placed on the head of a wearer, however, the top panel 214 and the sidewall 212 can stretch to generally conform to the shape of the wearer's head. Accordingly, the head guard 210 can stretch to a convex-shaped configuration, which may be referred to as hemispherical, when being worn by a user. In its stretched configuration, the head guard 210 delivers a compressive force to the wearer's head in order to substantially maintain the position of the head guard 210 relative to the wearer's head.

Figure 10:
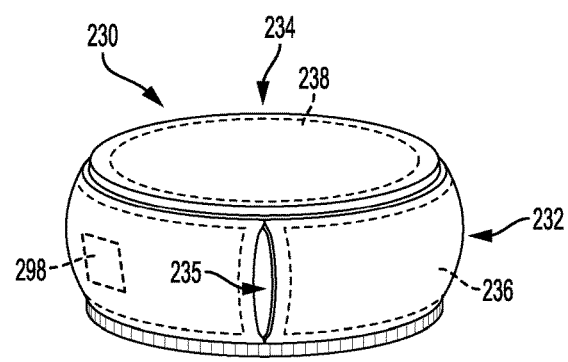
Figure 11:
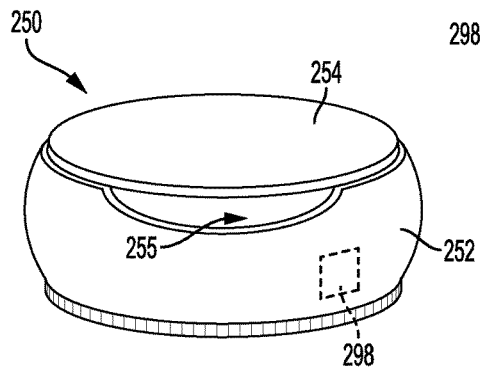

FIG. 10 illustrates a head guard 230 that defines an aperture 235. As with other embodiments, the aperture 235 is not limited to any particular configuration. In fact, a wide variety of aperture configurations can be utilized, such as a horizontal slit, a vertical slit, a vertically-oriented oblong opening, a horizontally-oriented oblong opening, a circular opening, or a rectangular opening, for example. The head guard 230 comprises a sidewall 232 and a top panel 234, each with an internal padding layer 236, 238. The padding layer 236 of the sidewall 232 extends circumferentially about the head guard with a gap that is aligned with the aperture 235. FIG. 11 illustrates a head guard 250 that comprises a sidewall 252 and a top panel 254. Similar to other embodiments, at least one of the sidewall 252 and the top panel 254 can comprise a padding layer. In this embodiment an aperture 255 is defined by the sidewall 252 and the top panel 254. Such configuration of the aperture 255 may be desirable, for example, to a wearer having dreadlocks. When the head guard 250 is placed on that wearer's head, the dreadlocks can be routed through the aperture 255.

Figure 12:
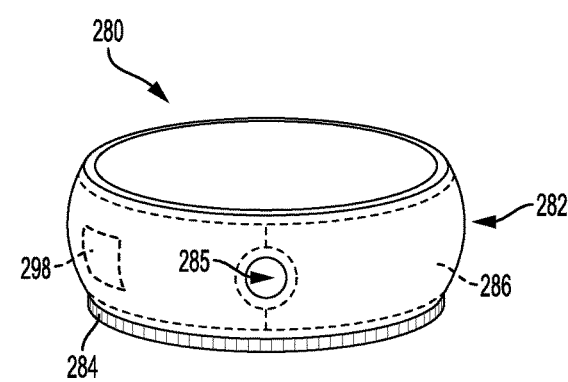
Figure 13:
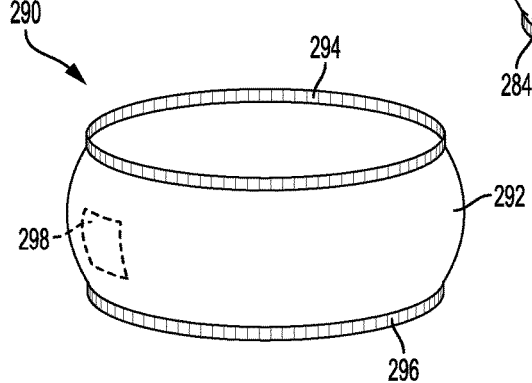
Figure 14:
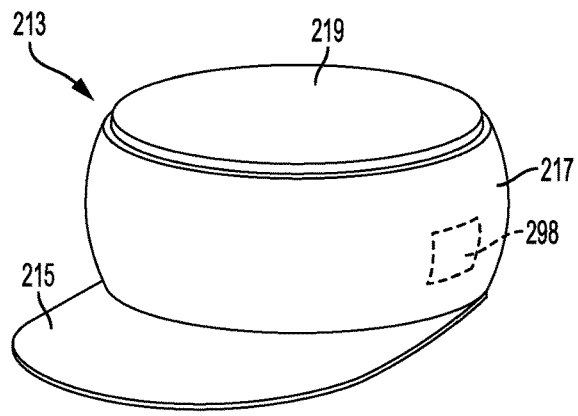

FIG. 12 illustrates a head guard 280 having a band-like configuration, as it does not include a top panel. A sidewall 282 comprises a padding layer 286 that extends circumferentially about the head guard 280 and an elastic portion 284 positioned proximate to an opening defined by the sidewall 282. The head guard 280 defines an aperture 285. As illustrated, the padding layer 286 is configured to have a gap which aligns with the aperture 285. While the head guard 280 in FIG. 12 has one elastic portion 284, other embodiments can utilize additional elastic portions, as illustrated by the head guard 290 in FIG. 13, for example. The head guard 290 has a band-like configuration, with a top opening and a bottom opening defined by a sidewall 292. A first elastic portion 294 is positioned proximate to the top opening and a second elastic portion 296 is positioned proximate to the bottom opening. Head guards having a band-like configuration can be worn by a user, for example, participating in a non-contact sport or other type of non-contact physical endeavor.

In some embodiments, additional components can be incorporated into the head guard. The head guard 213 illustrated in FIG. 14, for example, includes a brim 215 that is attached to a sidewall 217. While the head guard 213 is shown with a top panel 219, other band-like embodiments can also include a brim 215. Further, the brim can be in any suitable arrangement, such as a generally rigid visor having a cardboard core or a relatively soft visor, such as a lip comprised of fabric, or any other suitable type of bill.

Figure 15:
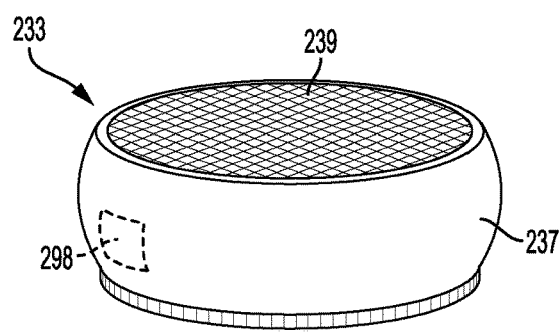

FIG. 15 illustrates yet another example embodiment of a head guard 233. The head guard 233 comprises a side wall 237 which can include a padding layer and a top panel 239. In the illustrated embodiment, the top panel 239 comprises a mesh portion to provide added airflow and ventilation to a wearer's head. Some embodiments incorporating a mesh top panel 239 utilize a top padding layer, while others do not. Additionally, or alternatively, the sidewall 237 can be mesh, or at least comprise one or more portions that are mesh or otherwise provide air flow to the wear.

Figure 16A:
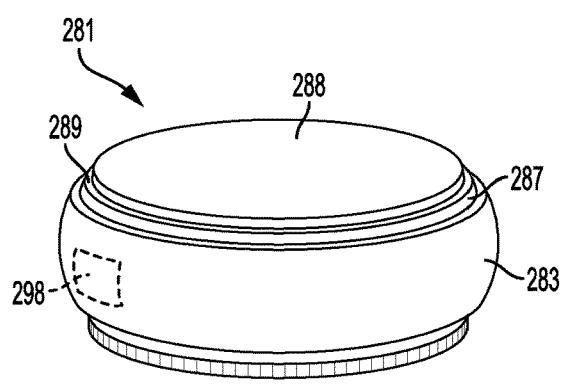
Figure 16B:
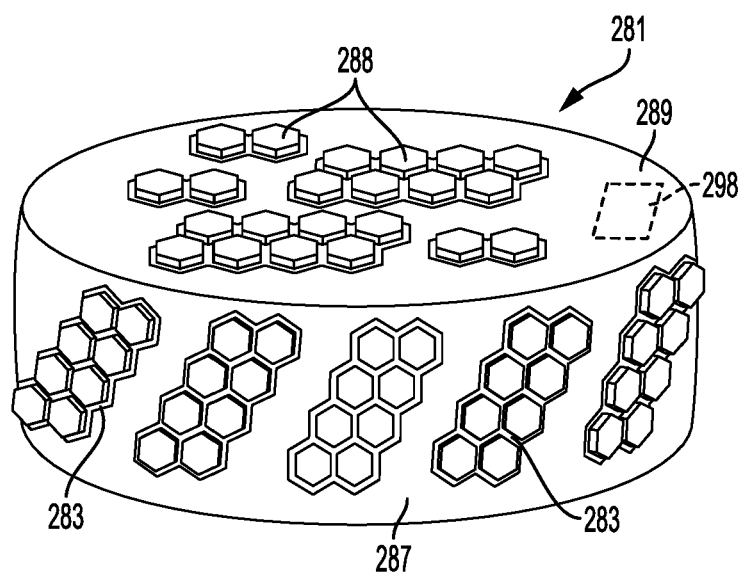
Figure 16C:
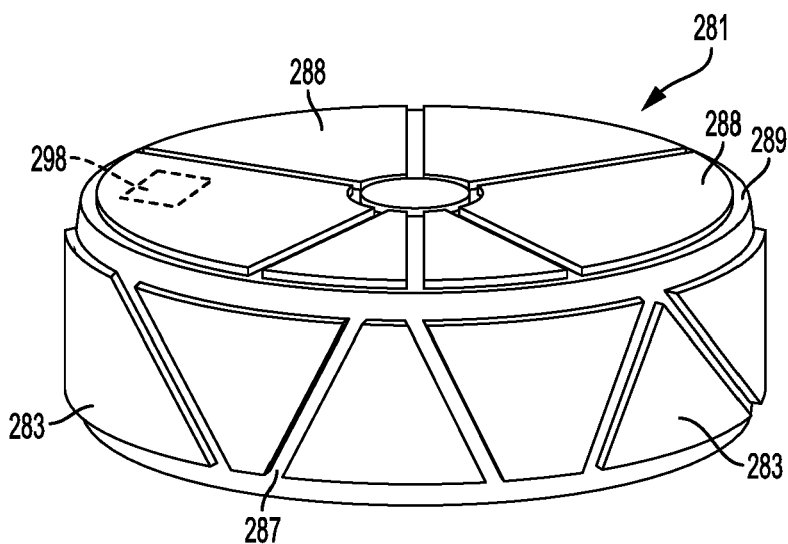

The particular orientation, location, and/or placement of the padding layer can vary. In some embodiments, for example, the padding layer is positioned within a pocket defined by two fabric layers. In other embodiments, the padding layer can be exposed, either internally or externally. FIG. 16A-16C illustrate example configurations of a head guard 281 that includes an external side padding layer 283 and an external top padding layer 288. The side padding layer 283 is attached to a side panel 287 to collectively define a sidewall and the top padding layer 288 is coupled to a top layer 289 to collectively define a top panel. FIG. 16A illustrates that the side padding payer 283 and the top padding layer 288 can be of unitary construction. FIG. 16B illustrates that the side padding payer 283 and the top padding layer 288 can be a collection of individual modules or pods that are attached to the top layer 289 and the side panel 287. FIG. 16C illustrates that the side padding payer 283 and the top padding layer 288 can be stitched, or otherwise molded or shaped to form a pattern. As is to be appreciated, any suitable technique can be used to couple the padding layers to the head guard 281, such as using stitching or using adhesives, such as glue, for example.

It is noted that while various head guards are illustrated having an elastic member around the lower periphery, such elastic members are not necessary for some configurations. Instead, the head guard can have compressive qualities or characteristics that maintain the head guard on the wearer's head. In other words, some or all of the head guard can be manufactured from stretchable materials that allow the head guard to stretch when placed on the head of a user and contract when removed from the head of a user. In some embodiments, the head guard can have one or more elastic members or portions and can also be stretchable.

Figure 17A:
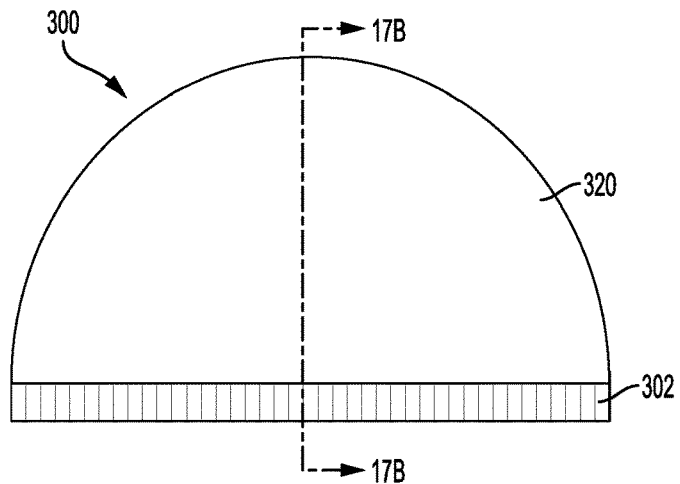
FIG. 17A shows a side view of an example head guard.
Figure 17B:
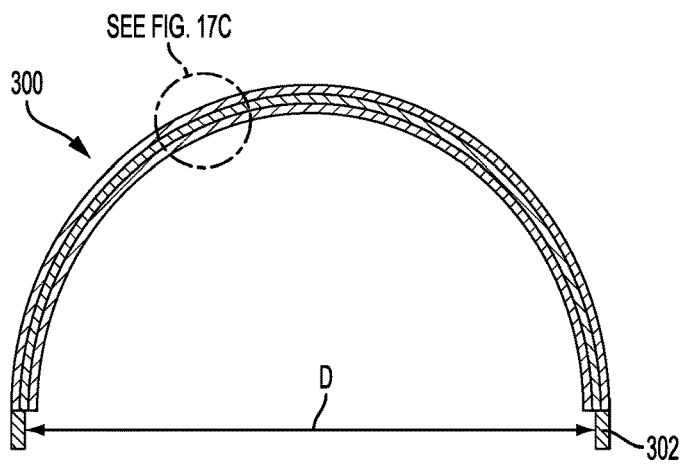
FIG. 17B shows a cross-sectional view taken along line 17B-17B of FIG. 17A.
Figure 17C:
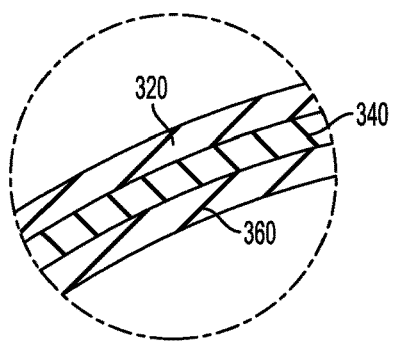
FIG. 17C is an enlarged view of the encircled portion of FIG. 17B.

Referring now to FIGS. 17A-17C, a head guard 300 in accordance with one non-limiting embodiment is shown. FIG. 17A shows a side view of the head guard 300 which has an elastic member 302 positioned around its lower periphery. The elastic member 302 can be an elastic band positioned inside a hem, for example. In some embodiments, an elastic member can be fed through hoops or other retention members. FIG. 17B shows a cross-sectional view of the head guard 300 taken along line 17B-17B of FIG. 17A. FIG. 17C shows an enlarged view of the encircled area of FIG. 17B and illustrates various layers of the head guard 300. As shown in FIGS. 17A-17C the head guard 300 of the illustrated embodiment comprises an outer layer 320, a padding layer 340, and an inner layer 360. In some embodiments, the head guard may be constructed with only an outer layer and padding layer, while in other embodiments the head guard may be constructed with only a padding layer and inner layer.

The head guard 300, or other head guards described herein, can define an internal diameter "D" (FIG. 17B), which can be selected to accommodate a particular type of user, such as a child, an adult, a person with a lot of hair, a person with short hair, and so forth. Thus, in certain embodiments, the head guard 300 can be manufactured to accommodate a child's head. In other embodiments, the head guard 300 can be manufactured to accommodate an adult's head. In other embodiments, the head guard 300 can be configured to accommodate both smaller-sized heads and larger-sized heads. In some embodiments, the value of "D" for adult head guards can be based on Table 1, below, and the value of "D" for child head guards can be based on Table 2, below.

TABLE 1

Adult Head Guard Example Sizes

| Diameter "D" | Size | Stretch Fit/Adjustable |
|---|---|---|
| 6¾ | Small (S) | |
| 6⅞ | | |
| 7 | Medium (M) | One Size Fits Most |
| 7⅛ | | |
| 7¼ | Large (L) | |
| 7⅜ | | |
| 7½ | XL | |
| 7⅝ | | |
| 7¾ | XXL | |
| 7⅞ | | |
| 8 | | |

TABLE 2

Child Head Guard Example Sizes

| Diameter "D" | Size | Stretch Fitted | Kids |
|---|---|---|---|
| 6 | XSM | | Infant |
| 6⅛ | S | | Toddler |

TABLE 2-continued

Child Head Guard Example Sizes

| Diameter "D" | Size | Stretch Fitted | Kids |
|---|---|---|---|
| 6¼ | | S/M | |
| 6⅜ | M | | Child |
| 6½ | | | |
| 6⅝ | L | L/X | Youth |
| 6¾ | | | |
| 6⅞ | XL | | |
| 7 | | | |

The padding layer utilized by head guards in accordance with the present disclosure can be comprised of any suitable material that provides the desirable characteristics and response to impact. For example, the padding layer can comprise one or more of the following materials: thermoplastic polyurethane (available, for example, from Skydex Technologies), military-grade materials, impact absorbing silicone, D30® impact absorbing material, impact gel, wovens, non-wovens, cotton, elastomers, IMPAXX® energy-absorbing foam (available from Dow Automotive), DEFLEXION shock absorbing material (available from Dow Corning), styrofoam, polymer gels, general shock absorbing elastomers, visco-elastic polymers, PORON® XRD impact protection (available from Rogers Corporation), Sorbothane® (available from Sorbothane Inc.), Neoprene (available from DuPont), Ethyl Vinyl Acetate, impact-dispersing gels, foams, rubbers, and so forth. The padding layer can be breathable and/or generally porous to provide ventilation. In some embodiments, the padding layer is a mesh material that aids in the breathability of the associated head guard. The padding layer can be attached to one or more layers (such as the outer layer 320 and the inner layer 360 of FIG. 17C, for example). In some embodiments, the padding layer 340 can be generally disconnected and "floating" between the layers. In some embodiments, the padding layer is attached to an elastic member or other portions of the head guard.

In some embodiments, padding layers in accordance with the present systems and methods can comprise a rate dependent material, such as a rate dependent low density foam material. Examples of suitable low density foams include polyester and polyether polyurethane foams. In some embodiments, such foams to have a density ranging from about 5 to about 35 pounds per cubic foot (pcf), more particularly from about 10 to about 30 pcf, and more particularly still from about 15 to about 25 pcf. PORON® and PORON XRD® are available from Rogers Corporation, which are open cell, microcellular polyurethane foams, is an example of one suitable rate dependent foam. However, in order to provide impact resistance, the padding layer can be any suitable energy absorbing or rate dependent materials. As such, other rate dependent foams or other types of materials can be used without departing from the scope of the present disclosure.

The other layers of head guards in accordance with the present disclosure can either be the same material or different material. The material can be, for example, and without limitation, polyester, nylon, spandex, ELASTENE (available from Dow Chemical), cotton, materials that glow in the dark or are fluorescent, and so forth. Either of the inner or outer layers can also be of a mesh or otherwise porous material. In some embodiments, the inner and/or outer layers can be a blend of a variety of materials, such as a spandex/polyester blend. In some embodiments, the head guard is water proof, water resistant, or water repellant. Other durable materials can be used for the outer layer of any embodiment, including knit, woven and nonwoven fabrics, leather, vinyl or any other suitable material. In some instances, it can be desirable to use materials for the layer than are somewhat elastic; therefore, stretchable fabrics, such as spandex fabrics, can be desirable. Such materials can help provide compressive forces to maintain placement of head guard on a wearer's head without the need for a chin strap, for example.

Various head guards in accordance with the systems and methods described herein can be manufactured with or otherwise include various coatings, agents, or treatments to provide anti-microbial or anti-bacterial properties. Some embodiments, for example, can utilize Microban® offered by Microban International, Ltd. for antibacterial protection. In some embodiments, the padding layer comprises antimicrobial agents and one or more other fabric layers of the head guard also treated with antimicrobial agents. Antimicrobial protection for the fabric layers can be in the form of a chemical coating applied to the fabric, for example. Generally, antimicrobial technologies combat odor by fighting bacteria resulting in fresher smell for longer and minimizing the frequency of laundering or washing. Any suitable technique can be used to provide head guards with antimicrobial properties. In one embodiment, for example, AEGIS Microbe Shield® offered by DOW Corning Corp. is utilized. Other examples of antimicrobial agents include SILVADUR® offered by The Dow Chemical Company is utilized, Smart Silver offered by NanoHorizons, Inc., and HealthGuard® Premium Protection offered by HealthGuard.

In some embodiments, a head guard, or at least various components of a head guard are configured to provide moisture wicking properties. Generally, moisture wicking translates into sweat management, which works by removing perspiration from the skin in an attempt to cool the wearer. Any suitable moisture wicking can be used. In one embodiment, a topical application of a moisture wicking treatment to a fabric of the head guard is utilized. The topical treatment is applied to give the head guard the ability to absorb sweat. The hydrophilic (water-absorbing) finish or treatment generally allows the head guard to absorb residue, while the hydrophobic (water-repellent) fibers of the head guard help it to dry fast, keeping the wearer more comfortable. In one embodiment, the blend of fiber is used to deliver moisture wicking properties by combining a blend of both hydrophobic (such as polyester) with hydrophilic fibers. Certain blends of these fibers allow the hydrophilic fibers to absorb fluid, moving it over a large surface area, while the hydrophobic fibers speed drying time. One benefit of head guards utilizing these types of fiber blends is that moisture management properties are inherent in the fiber blend, meaning they will never wash or wear out.

Figure 18A:
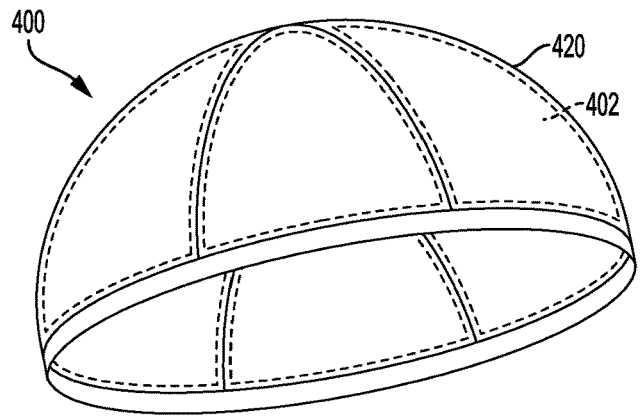
FIG. 18A is a perspective view of an example head guard.
Figure 18B:
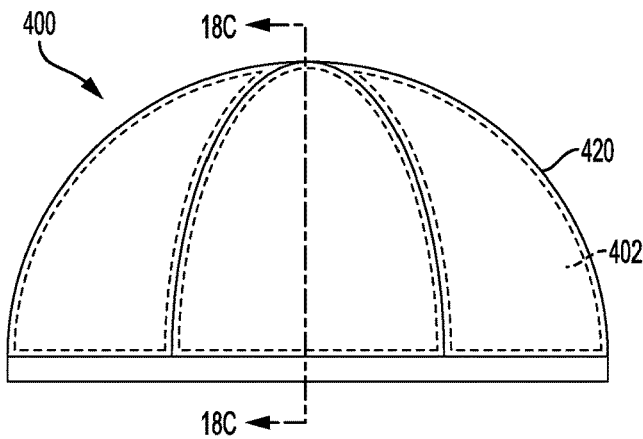
FIG. 18B shows a side view of the head guard of FIG. 18A.
Figure 18C:
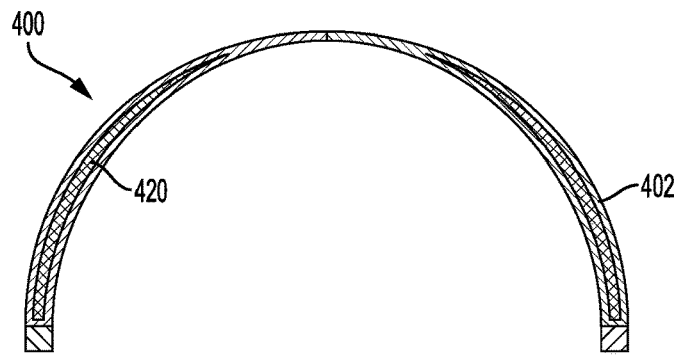
FIG. 18C shows a cross-sectional view taken along line 18C-18C of FIG. 18B.

FIGS. 18A-18C illustrate a head guard 400 in accordance with various non-limiting embodiments. FIG. 18A is a perspective view of the head guard 400, which comprises a plurality of panels 402. The panels 402 can be arranged such that the head guard 400 is generally a convexshape. FIG. 18B is a side view of the head guard 400 and FIG. 18C is a cross-sectional view of the head guard 400 of FIG. 18B taken along line 18C-18C. As shown in FIG. 18C, each panel 402 may include an inner pocket. Padding 420 can be positioned within the inner pocket of each panel 402. In some embodiments, padding 420 can semi-rigid (such as Styrofoam), while other embodiments can utilize flexible or generally pliable padding 420.

Figure 19:
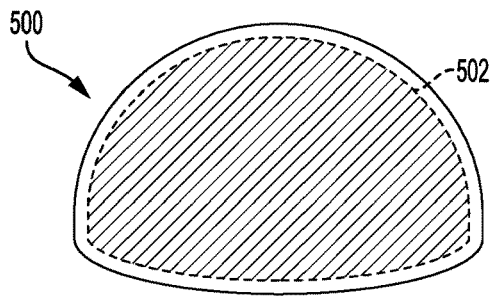
FIGS. 19-21 show example arrangements of padding within example head guards.
Figure 20:
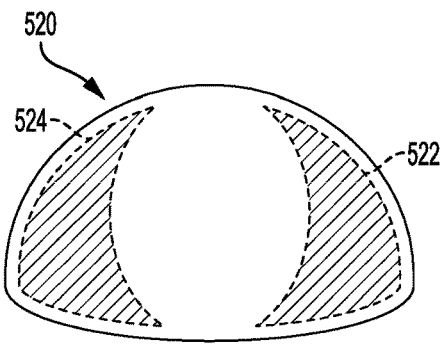
Figure 21:
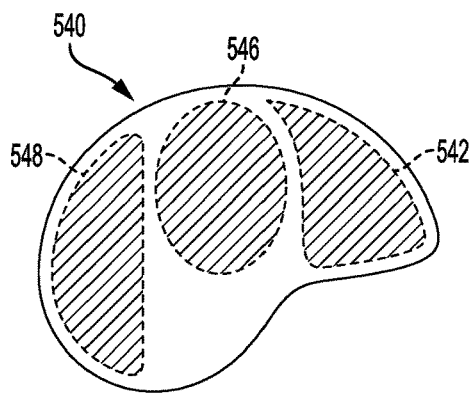

The arrangement or placement of the padding within the head guard can vary. FIGS. 19-21 illustrate non-limiting embodiments of head guards having a variety of padding orientations. The head guard 500 shown in FIG. 19, for example, shows a padding layer 502 that is generally convex-shaped. The head guard 520 shown in FIG. 20 shows a first padding 522 positioned at a first position and a second padding 524 positioned at a second position. The head guard 540 shown in FIG. 21 shows a plurality of different padding layer types arranged at various positions on the head guard 540. As illustrated, a first padding is positioned at first padding layer 542 and a second padding is positioned at second padding layer 548. A third padding is positioned at third padding layer 546. The third padding layer 546 can be, for example, a different type of padding material than the padding material of the first and second padding layers 542, 548. The first and second padding layers 542, 548 can be a semi-rigid padding (such as Styrofoam) while the third padding layer 546 is can be a pliable or semi-pliable layer. In some embodiments, the placement or configuration of the padding can depend on the type of helmet a user may wear in combination with the head guard. The padding layers 502, 522, 542, 546, and 548 can be any suitable type of material, such as, without limitation, one or more of the materials described above with reference to padding layer 340.

Figure 22:
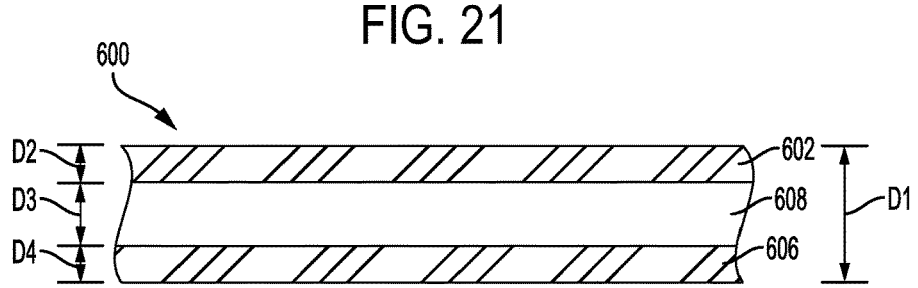
FIG. 22 shows a cross-sectional view of a head guard in accordance with one non-limiting embodiment.

FIG. 22 illustrates a cross-sectional view of a head guard 600 in accordance with one non-limiting embodiment. The head guard 600 comprises an outer layer 602, and inner layer 606, and a padding layer 608. Each of the layers can be manufactured from a wide variety of materials, as described above. The overall thickness (D1) of the head guard 600 can vary based on application. In some embodiments, for example, D1 can be in the range of about 0.1" to about 0.5". In some embodiments, for example, D1 can be in the range of about 0.5" to about 1.0". In some embodiments, for example, D1 can be larger than about 1.0". The thickness can be based on, for example, the type of helmet worn with the head guard (if any), the type of sport being played while wearing the head guard, or characteristics of the wearer. While FIG. 22 shows three layers, this disclosure is not so limited. As is to be appreciated, in some embodiments, head guards can have more or less layers. For example, various head guards may not utilize an inner layer. In any event, FIG. 22 shows the respective thicknesses of the outer layer 602 (D2), the padding layer 608 (D3), and the inner layer 606 (D4). In some embodiments, each of D2, D3, and D4 are generally equal. In some embodiments, D2 and D4 are generally equal while D3 differs. In some embodiments, two of the layers have similar thickness while the third layer differs. In some embodiments, all three layers have different thicknesses. In any event, D2, D3, and D4 can each be any suitable thickness. For example, the thickness of any layer can be less than about 0.01", the thickness of any layer can be in the range of about 0.01" to about 0.125", or the thickness of any layer can be in range of about 0.125" to 0.5". In some embodiments, the thickness of any layer can be greater than 0.5". Moreover, in some embodiments, the thickness of the padding layer is greater than about 30% of the thickness D1. In some embodiments, the thickness of the padding layer is greater than about 50% of the thickness D1. In some embodiments, the thickness of the padding layer is greater than about 70% of the thickness D1. In some embodiments, the thickness of the padding layer is greater than about 90% of the thickness D1. In some embodiments, the thickness of the padding layer is greater than about 99% of the thickness D1.

In some embodiments the padding layer 608 is disconnected from the outer layer 602 and inner layer 606, such that it is generally "floating" between the two. In other embodiments the padding layer 608, or at least portions thereof, is attached to one or both of the outer layer 602 and inner layer 606. Finally, it is noted that while FIG. 22 shows each layer having a generally uniform thickness, this disclosure is not so limited. In fact, the thickness of any particular layer may vary at different locations of the head guard 600. For example, the thickness of the padding layer 608 may be thicker at a first location of the head guard 600 and thinner at a second location of the head guard 600.

Figure 23:
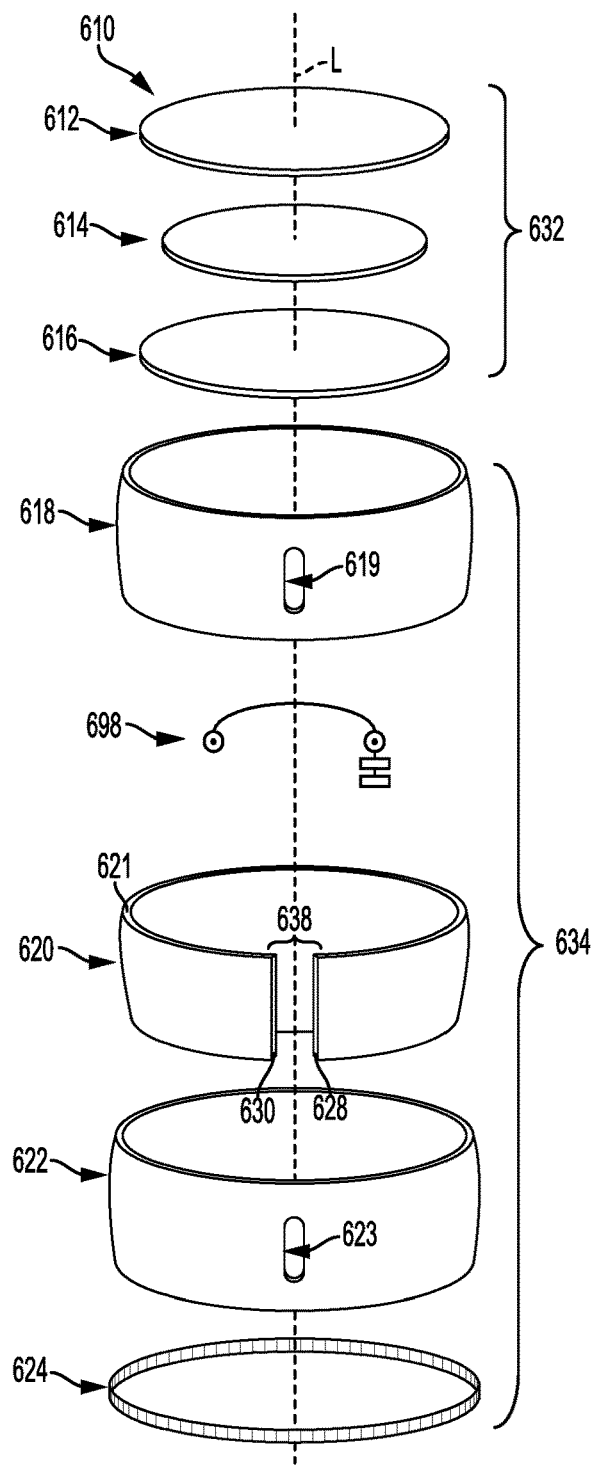
FIG. 23 shows an exploded view of a head guard in accordance with one non-limiting embodiment.

FIG. 23 is an exploded view of a head guard 610 in accordance with one non-limiting embodiment. The head guard 610 has a longitudinal axis "L" and comprises a multi-layered top panel 632 and a multi-layered sidewall 634. The multi-layered top panel 632 can be attached to the multi-layered sidewall 634 using suitable stitching techniques, for example. The multi-layered top panel 632 comprises a top fabric layer 612 and a bottom fabric layer 616. The multi-layered top panel 632 can be generally flat-shaped with the head guard 610 is in a relaxed configuration. The multi-layered top panel 632 can be generally convex-shaped with the head guard 610 is in an expanded configuration. The top fabric layer 612 and the bottom fabric layer 616 can be manufactured from a stretchable material, as described in more detail below. A padding layer 614 is positioned between the top fabric layer 612 and the bottom fabric layer 616. In some embodiments, the surface area of the padding layer 614 is slightly smaller than the surface area of the top fabric layer 612. Furthermore, the padding layer 614 can also be stretchable, though not necessarily as stretchable as the top fabric layer 612 and the bottom fabric layer 616. The top fabric layer 612 and the bottom fabric layer 616 can cooperate to define a pocket, with the padding layer 614 positioned in the pocket.

In the illustrated embodiment, the multi-layered sidewall 634 comprises an inner fabric layer 618, a padding layer 620, an outer fabric layer 622, and an elastic member 624. The multi-layered sidewall 634 can be generally cylindrical-shaped with the head guard 610 is in a relaxed configuration. The multi-layered sidewall 634 can be generally frustoconically-shaped with the head guard 610 is in an expanded configuration. The inner fabric layer 618 and the outer fabric layer 622 can be manufactured from a stretchable material, as described in more detail below. The inner fabric layer 618 can define an aperture 619 having any suitable size, configuration, or arrangement. The outer fabric layer 622 can define an aperture 623 having any suitable size, configuration, or arrangement that generally aligns with the aperture 619 when the head guard 610 is an assembled configuration. Furthermore, stitching or other attachment techniques can be used to join the periphery of the aperture 619 with the periphery of the aperture 23 in the assembled configuration. The side padding layer 620 is positioned between the inner fabric layer 618 and the outer fabric layer 622. In some embodiments, the surface area of the padding layer 620 is slightly smaller than the surface area of the outer fabric layer 622. Furthermore, the side padding layer 620 can also be stretchable, though not necessarily as stretchable as the inner fabric layer 618 and the outer fabric layer 622. The inner fabric layer 618 and the outer fabric layer 622 can cooperate to define a pocket, with the side padding layer 620 positioned in the pocket. In some embodiments, the inner fabric layer 618 and the outer fabric layer 622 are attached in an arrangement that forms a plurality of pockets and a padding layer is positioned within each pocket such that a collection of individual padding modules or pods generally forms the padding layer.

Figure 28:
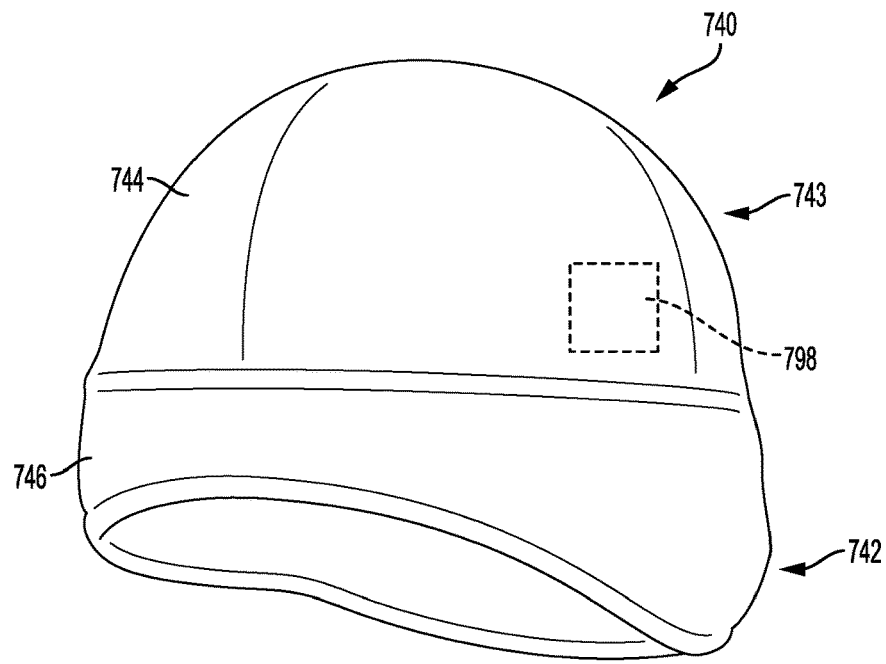
FIG. 28-29 show example having a non-stick external surface.
Figure 29:
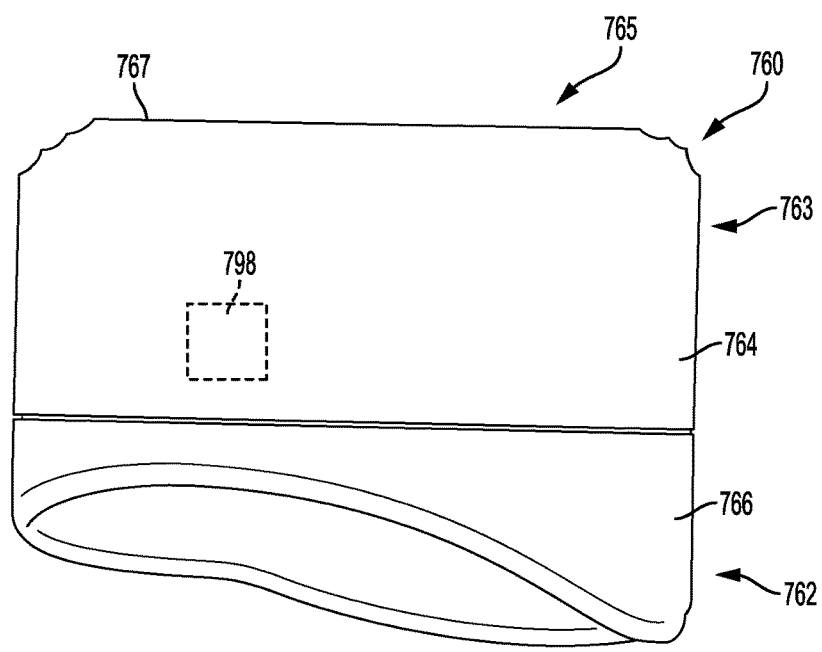

The side padding layer 620 can be the same or different material as the padding layer 614. Further, these two layers can have the same or different thicknesses. The side padding layer 620 can be any suitable shape or configuration. In the illustrated example, the side padding layer 620 has a top surface 621, a first end surface 630, a second end surface 628, and a bottom surface (not shown). While the side padding layer 620 is illustrated as being generally rectangular and circumferentially extending about the head guard 610, other embodiments can utilize side padding layers 620 having different shapes. In any event, in the assembled configuration, the top surface 621 is positioned proximate to the multi-layered top panel 632. The first end surface 630 and the second end surface 628 can be opposed and circumferentially spaced to define a gap 638. While the gap 638 is shown as being generally rectangular, the gap 638 can have any suitable shape or size. In some embodiments, the gap 638 is positioned such that it generally aligns with the aperture 619 defined by the inner layer 618 and the aperture 622 defined by the outer layer 622. In other embodiments, the first end surface 630 and the second end surface 628 are joined together to form a contiguous ring of padding. Moreover, in some embodiments, the padding layer 620 can generally be a contiguous ring of padding that also defines an aperture therethrough. It is noted that as with other head guards illustrated herein, the head guard 610 shown in FIG. 23 is merely an illustrative example embodiment. Thus, while the lower periphery of the head guard 610 is illustrated being flat, other embodiments of head guards can have different shapes and configurations without departing from the scope of the present disclosure. For example, some embodiments of the head guard 610 can include a lower periphery having a wave-like configuration, such that the side and rear part of the multi-layered sidewall 634 extend further from the multi-layered top panel 632 to cover a user's ears and wrap around the back of their head, as shown in FIGS. 28-29, for example.

Headband-style head guards in accordance with the present disclosure can also incorporate a sensory input and communications system 698. The sensory input and communications system 698 can include any suitable number of sensors, each sensor being of any suitable type. Additional detail regarding example sensory input and communications system is discussed below with regard to FIGS. 42-47

Figure 24:
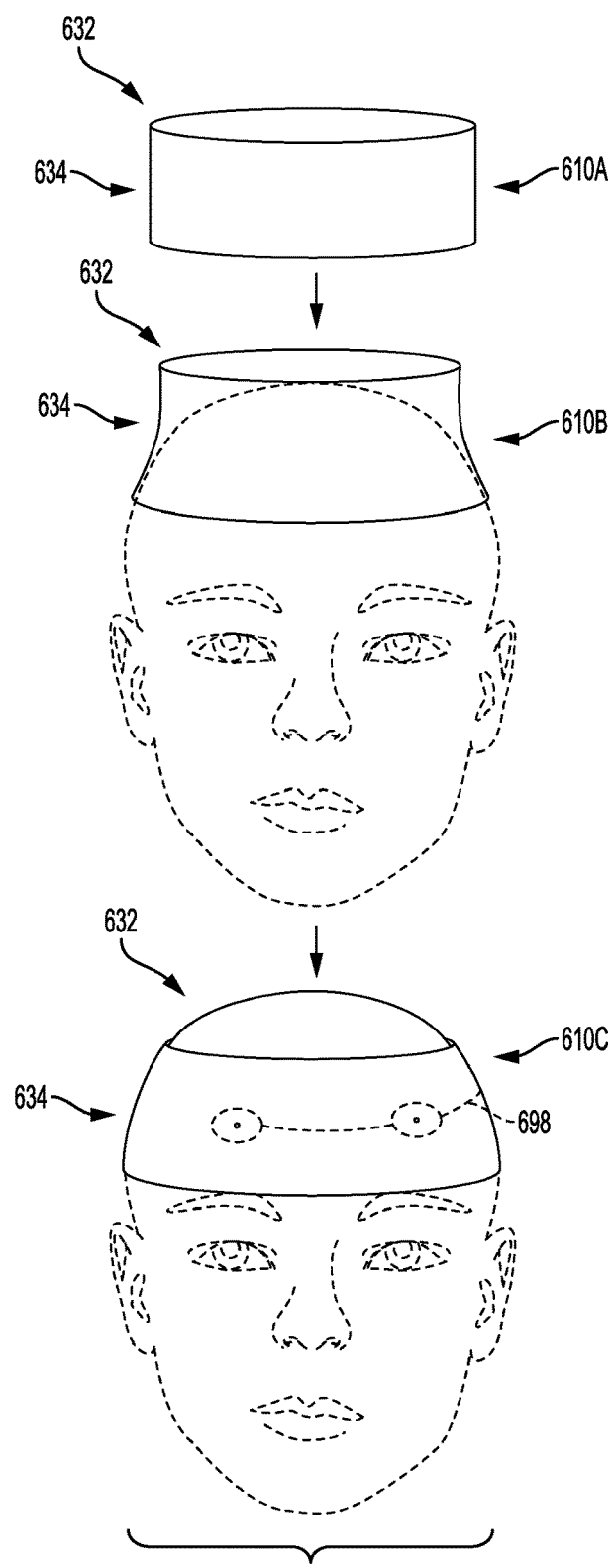
FIG. 24 depicts the head guard of FIG. 23 being positioned on the head of a wearer and stretching from a relaxed configuration to an expanded configuration.

FIG. 24 depicts the head guard 610 shown in FIG. 23 stretching from a relaxed configuration shown by the head guard 610A to an expanded configuration by the head guard 610C. As shown, head guard 610A in generally cylindrical in the relaxed configuration. As head guard is placed on the head of a wearer, the multi-layered sidewall 634 begins to expand, as shown by head guard 61013. As the head of the wearer is inserted further into the head guard, the head guard continues to stretch until it reaches an expand configuration, shown by head guard 610C. As shown by head guard 610C, the multi-layered top panel 632 changes from a flat shape to a convexshape when the head guard is placed on wearer's head. Additionally, the multi-layered sidewall 634 also changes shape in order to accommodate the wearer's head. As is to be appreciated, due to the stretchability of the head guard 610, it can accommodate a range of head sizes and shapes. When the head guard 610C is removed from the wearer's head, it will return to the shape illustrated by head guard 610A.

Figure 25:
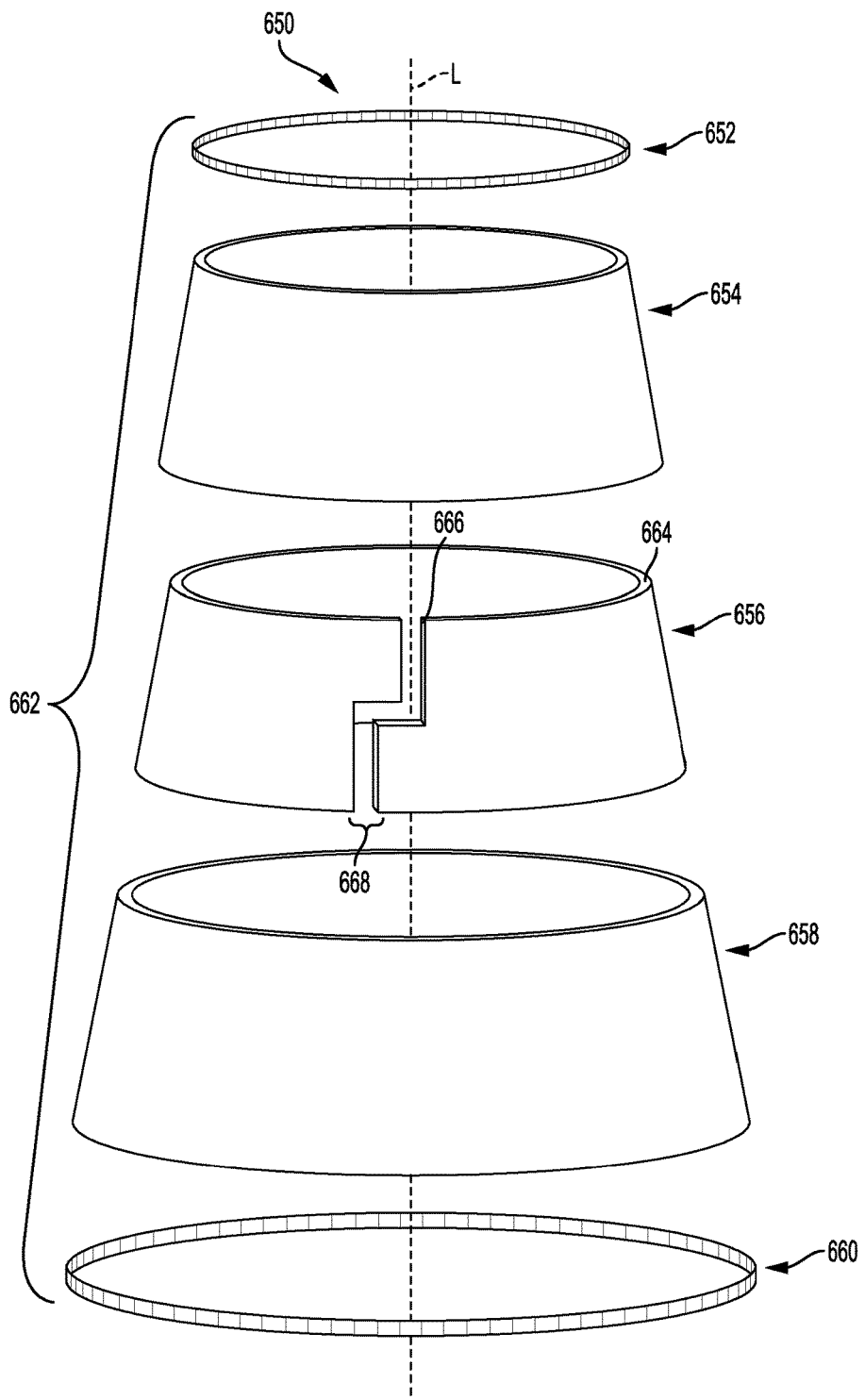
FIG. 25 shows an exploded view of a head guard in accordance with one non-limiting embodiment.

FIG. 25 is an exploded view of a band-like head guard 650 in accordance with one non-limiting embodiment. The head guard 650 has a longitudinal axis "L" and comprises a multi-layered side panel 662. The multi-layered sidewall 662 comprises an inner fabric layer 654, a padding layer 656, an outer fabric layer 658, and elastic members 652, 660. The multi-layered sidewall 662 of the illustrated embodiment is generally frustoconically-shaped with the head guard 650 is in a relaxed configuration. As is to be appreciated, other embodiments can have other shapes in the relaxed configuration, such as cylindrical or toroidal, for example.

The inner fabric layer 654 and the outer fabric layer 658 can be manufactured from a stretchable material, as described in more detail below. The padding layer 656 is positioned between the inner fabric layer 654 and the outer fabric layer 658. In some embodiments, the surface area of the padding layer 656 is slightly smaller than the surface area of the outer fabric layer 658. Furthermore, the padding layer 656 can also be stretchable, though not necessarily as stretchable as the inner fabric layer 654 and the outer fabric layer 658. The inner fabric layer 654 and the outer fabric layer 622 can cooperate to define a pocket, with the padding layer 656 positioned in the pocket.

The padding layer 656 can be any suitable shape or configuration. In the illustrated example, the padding layer 656 has a top surface 664, a first end surface 666, a second end surface (not shown), and a bottom surface (not shown). In the assembled configuration, the top surface 664 is positioned proximate to elastic member 652 and the bottom surface is positioned proximate to the elastic member 660. The first end surface 660 and the second end surface can be opposed and circumferentially spaced to define a gap 668. The gap 668 can have any suitable shape or size. In some embodiments, the gap 668 is positioned such that it aligns with an aperture through the head guard. In other embodiments, the first end surface 666 and the second end surface 628 are joined together to form a contiguous ring of padding.

Figure 26A:
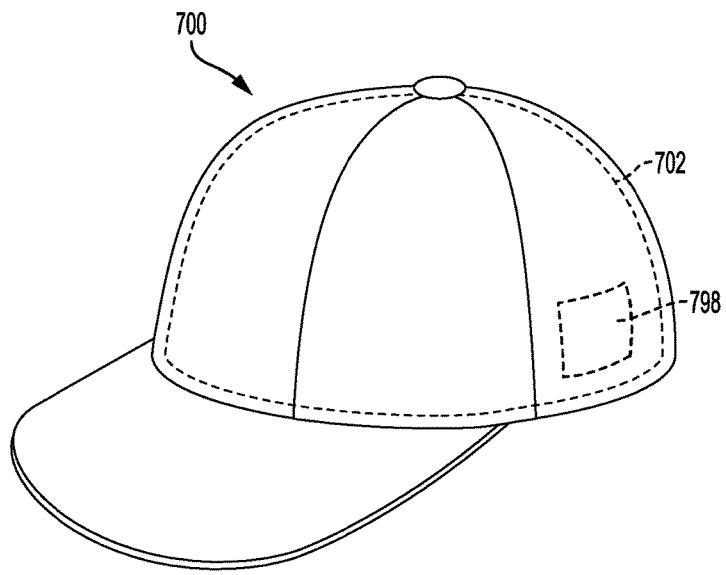
FIGS. 26A-27B show example baseball hats that incorporate a head guard.
Figure 26B:
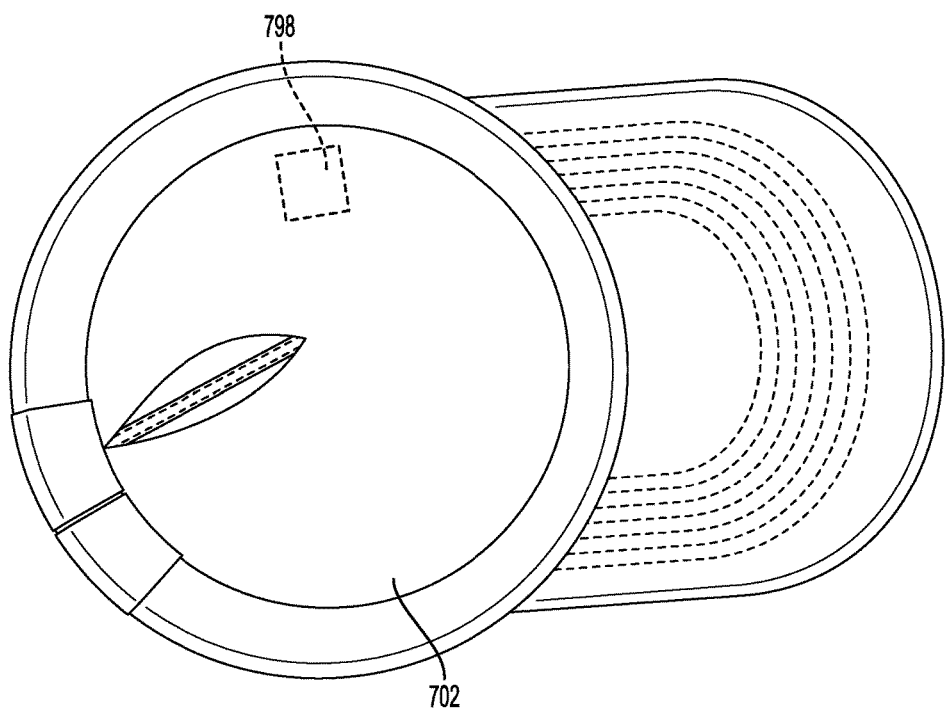

In some embodiments, head guards in accordance with the present disclosure can be integrated, incorporated, coupled to, formed with, or otherwise associated with various forms of headwear. For example, head guards can be built into baseball hats, softball hats, winter hats, cowboy hats, or other types of headwear. FIGS. 26A, 26B, 27A, and 27B illustrate baseball hats with built-in head guards in accordance with example embodiments, each of which also includes a sensory input and communications system 798. Referring first to FIGS. 26A and 26B, the baseball hat 700 includes a padding layer 702 that is generally convex-shaped. While the baseball hat 700 depicted in FIG. 26B does not illustrate an interior fabric layer, some embodiments can include an interior fabric layer. For example, the baseball hat 700 may be constructed with three layers, as illustrated in FIG. 22, for example.

Figure 27A:
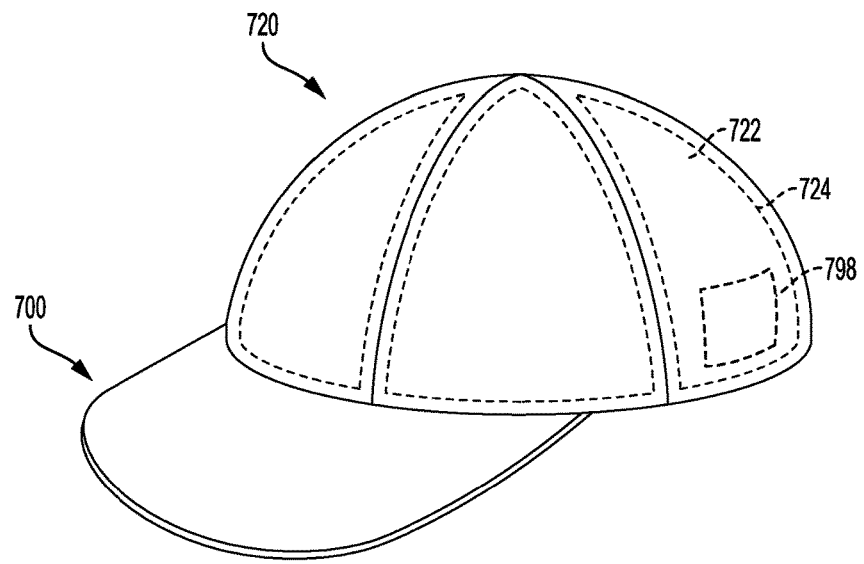
Figure 27B:
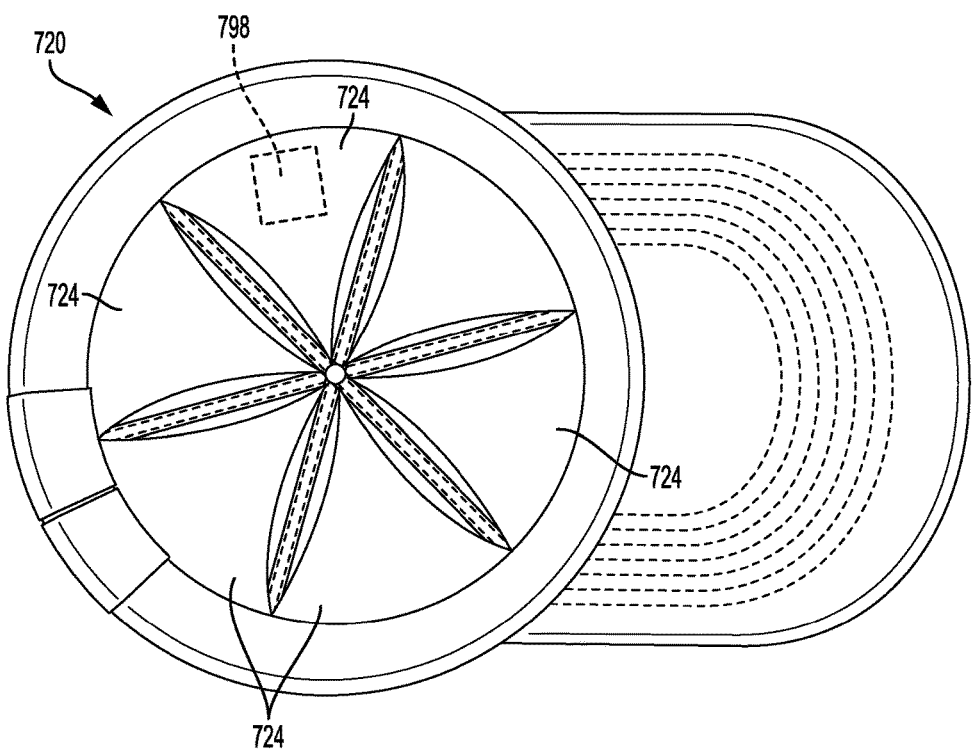

The baseball hat 720 of FIGS. 27A-27B comprises a plurality of panels 722 that are stitched together to form the hat. As illustrated, each individual panel 722 includes a padding layer 724. In some embodiments, each panel 722 forms an internal pocket that houses the padding layer 724. While the baseball hat 720 depicted in FIG. 27B does not illustrate an interior fabric layer, some embodiments can include an interior fabric layer. In some embodiments, the padding layer is discretely incorporated into the baseball hat. In other words, the baseball hat can have the general appearance of a baseball hat that does not include a padding layer. The padding layers 702 and 724 can be any suitable type of material, such as, without limitation, one or more of the materials described above with reference to padding layer 340. As is to be appreciated, a padding layer can be incorporated (discretely or otherwise) into other types of hats, such as, golf hats, visors, cowboy hats, police hats, fireman hats, military hats or head coverings, and so forth.

As illustrated in FIGS. 28-29, in some embodiments, a head guard can comprise a non-stick exterior surface. The head guard 740 shown in FIG. 28 comprises a multi-layer top panel 743 that is attached to (or integral with) a multi-layer lower panel 742. Each of the multi-layer top panel 743 and the multi-layer lower panel 742 can include a padding layer, as described above. Further, the multi-layer top panel 743 has an exterior surface 744 and the multi-layer lower panel 742 has an exterior surface 746. These exterior surfaces 744, 746 can come in direct contact with the interior surface of a helmet, or other type of head gear, when both pieces of gear are worn by the user at the same time. Referring now to FIG. 29, a head guard 760 is shown that comprises a multi-layer top panel 765 and a multi-layer side panel 763 that is attached to a multi-layer lower panel 762. Each of the multi-layer panels 762, 763, 765 can include a padding layer as described above. Further, the multi-layer top panel 765 has an exterior surface 767, the multi-layer side panel 763 has an exterior surface 764 and the multi-layer lower panel 762 has an exterior surface 766. These exterior surfaces 764, 766, 767 can come in direct contact with the interior surface of a rigid helmet when both pieces of gear are worn by the same user. The head guards illustrated in FIG. 28 and FIG. 29 are schematically shown to include a sensory input and communications system 798.

The exterior surfaces 744, 746, 764, 766, 767 can have non-stick (or non-slipstick) properties that generally reduces a coefficient of friction of the exterior surface of the head guard. While a variety of friction-reducing treatments or coatings can be used to provide the non-stick properties, in one example embodiment a Polytetrafluoroethylene (PTFE) treatment is used. Example PTFE treatments include the Teflon polymer products from DuPont (Teflon® PTFE fluoropolymer) and Chemfab from Saint Gobain. Beneficially, PTFE also provides repellency against oil- and waterbased stains, dust and dry oil. In some embodiments a topical application of a coating or film is used. In other embodiments, a PTFE fiber, such as a Teflon® PTFE fiber from DePont) can be integrated into the fabric (such as polyester or nylon) material mix. It is noted that in addition to other benefits, the lower panels 742, 762 can increase the amount of exterior surface area of the head guard that is treated with the non-stick coating.

Providing an exterior non-stick surface can be beneficial when the user wears the head guard in combination with a helmet. For example, due to the low coefficient of friction, the helmet will easily slide over top of the head guard when the user is putting on their helmet. Additionally, when the helmet receives an impact, the helmet can rotate relative to the head guard, perhaps only slightly, but thus resulting in less rotational movement for the wearer's head due to the rotational force generated by the impact. It is noted that while head guards 740 and 760 are configured to cover the top of a wearer's head, it is to be appreciated that similar configurations can be used for band-like head guards. As such, a band-like head guard can have non-stick properties and can also include a lower panel similar to those illustrated in FIG. 28-29.

Figure 30:
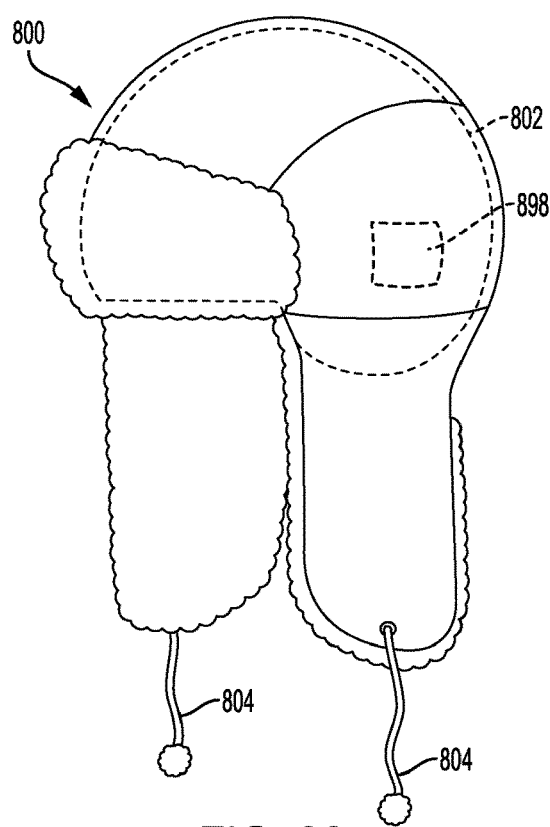
Figure 31:
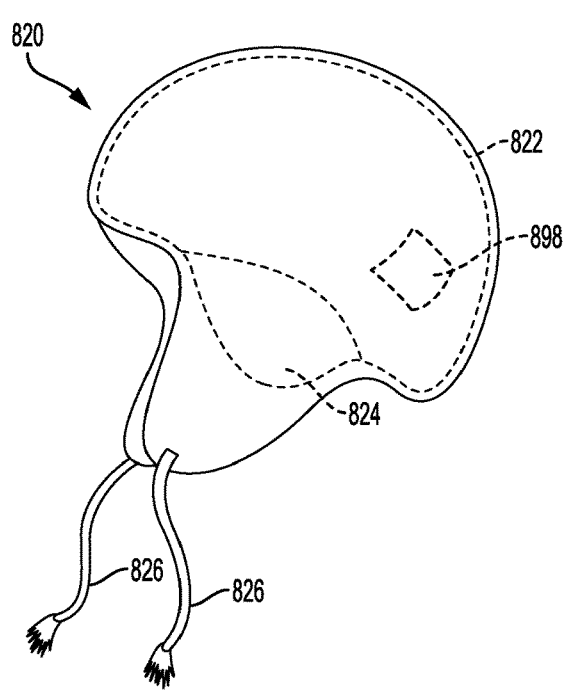

FIGS. 30-33 illustrate winter headgear incorporating head guards in accordance with various embodiments. In some embodiments, the padding layer is discretely incorporated into the winter hat. In other words, the winter hat can have the general appearance to an observer of a winter hat that does not include a padding layer. Each of the example winter headgear incorporates a head guard schematically shown to include a sensory input and communications system 898. Referring first to FIG. 30, Winter hat 800 is an aviator style hat having insulating properties. A padding layer 802 is incorporated into the structure of the winter hat 800. The padding layer 802 can be rigid, pliable, or a combination of rigid components and pliable components. The winter hat 800 can include chin straps 804 to secure the winter hat 800 to a wearer. The winter hat 800 can include a plurality of layers, such as an inner fur-lined layer, a middle padding layer, and an outer fabric layer. Additional insulating layers can also be used. Winter hat 820 shown in FIG. 31 is another style of winter headgear that incorporates a head guard. The head guard comprises a first padding layer 822 and a second padding layer 824. The particular material for the first padding layer 822 and the second padding layer 824 may differ. For example, a relatively thick padding can be used for first padding layer 822 while padding having high insulating properties can be used for second padding layer 824 due to its proximity to a wearer's ears. Winter hat 820 has chin straps 826 to allow a user to securely fasten the winter hat 820 to their head.

Figure 32:
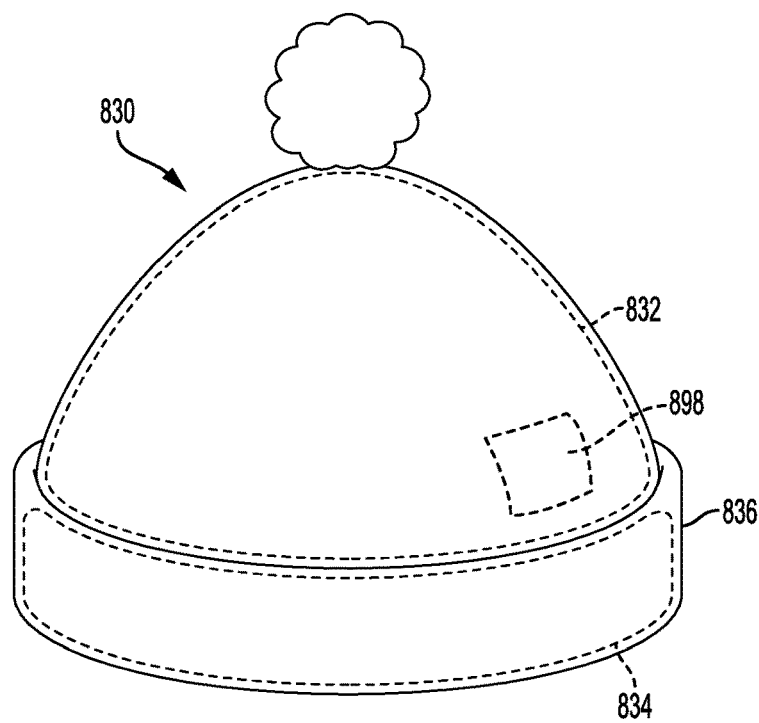
Figure 33:
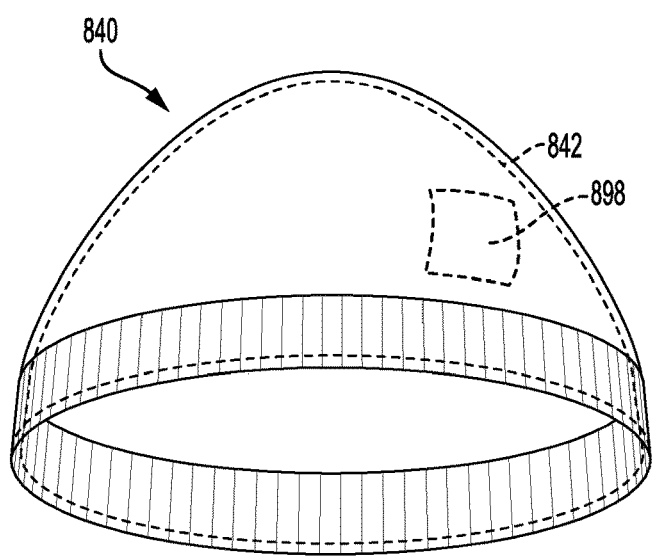

FIG. 32 is yet another embodiment showing a winter hat 830 that includes a first padding layer 832 and a second padding layer 834. The first padding layer 832 can be in a convex configuration and either be a single unitary piece or a plurality of components that form the generally convex-shape. In some embodiments, the first padding layer 832 does not form a complete dome, but instead is localized to certain areas, such as the front and the back of the hat, for example. As illustrated, the second padding layer 834 can be in the headband portion 836. The first and second padding layers 832, 834 can be manufactured from the same or different types of materials. For example, the first padding layer 832 can be Styrofoam while the second padding layer 834 can be an impact gel. Alternatively, both the first and second padding layers 832, 834 can both be impact gel. FIG. 33 shows another embodiment of a winter hat 840 that comprises a padding layer 842. As is to be appreciated, the present disclosure is not limited to any particular type or style of winter hat or winter head gear.

Figure 34A:
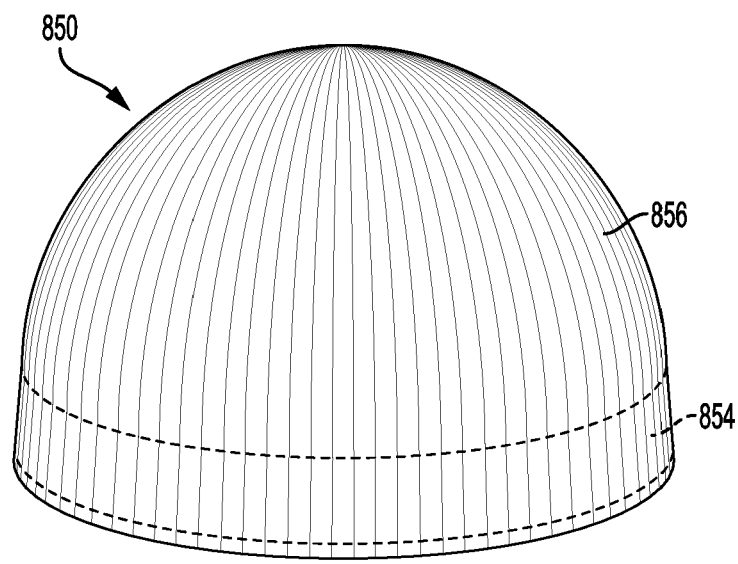
Figure 34B:
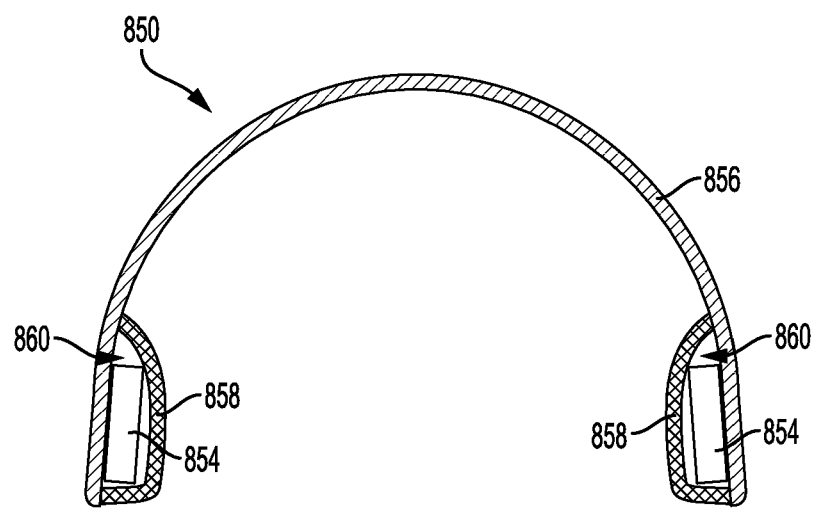
FIG. 34B shows a cross-sectional view of the winter hat of FIG. 34A.

FIG. 34A depicts another embodiment of a winter hat 850 that incorporates a padding layer 854. FIG. 34B is a cross-sectional view of the winter hat 850. The winter hat 850 can comprise a fabric layer 856 that is configured to cover a wearer's head. A thermal layer 858 can have a band-like configuration and be attached to an interior surface of the fabric layer to form a pocket 860. A padding layer 854 is positioned in the pocket 860. In some embodiments, the thermal layer 858 is an extension of the fabric layer 856 that is folded and stitched to create a pocket to house the padding layer 854.

Referring to FIGS. 30-34B, the padding layers 802, 822, 824, 832, 834, and 842, 854 can be any suitable type of material, such as, without limitation, one or more of the materials described above with reference to padding layer 340.

Figure 35:
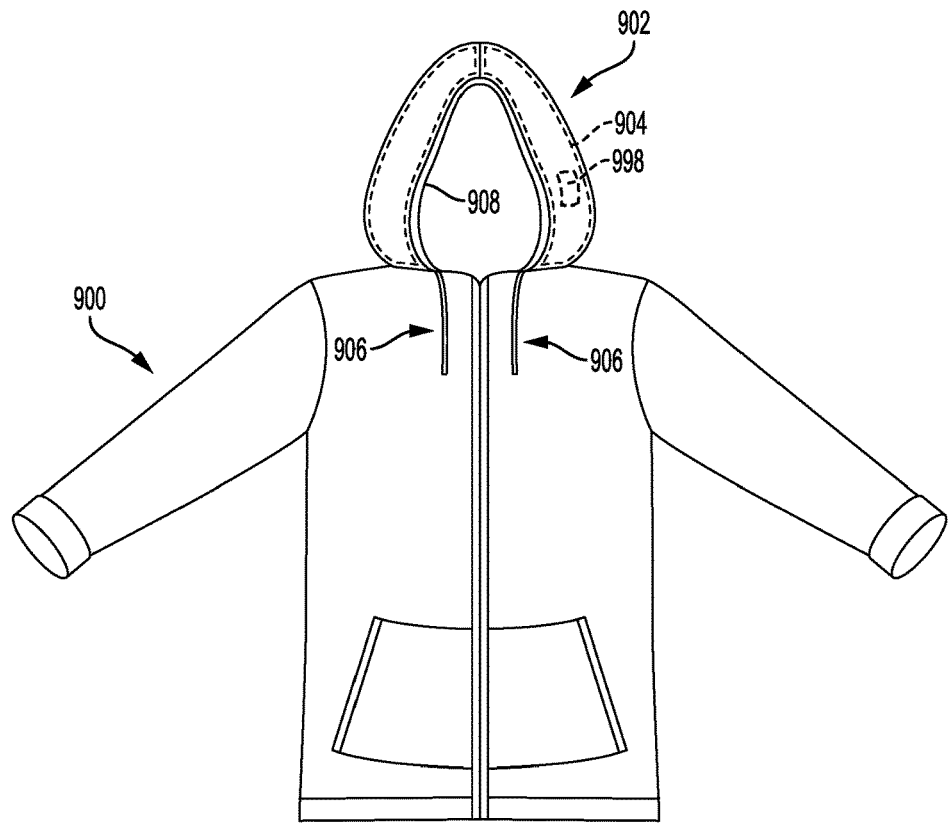
FIG. 35 shows an example hooded apparel that incorporates a head guard.

In some embodiments, head guards in accordance with the present disclosure can be integrated, incorporated, coupled to, formed with, or otherwise associated with various types of apparel. FIG. 35 illustrates an example embodiment of a hooded sweatshirt 900 that incorporates a head guard in its hood. The hooded sweatshirt 900 shown in FIG. 35 is for illustrative purposes only. In fact, the head guard could be incorporated into the hood of any form of apparel, such as a jacket, a pull-over sweatshirt, a windbreaker, a winter coat, or any other article of clothing with a hood. In any event, the hooded sweatshirt 900 has a hood 902 that includes a padding layer 904. The hood 902 can be constructed using any suitable technique, such as the three layer technique illustrated in FIG. 22. The hood 902 can be sized to generally conform closely to the wearer's head. In some embodiments, the padding layer 904 comprises a Styrofoam or other semi-rigid core. Drawstrings 906 can be routed through a hem 908 in the hood 902. By drawing the drawstrings 906 downward, the hood 902 can be positioned in close proximity to the wearer's head.

Figures 36, 37:
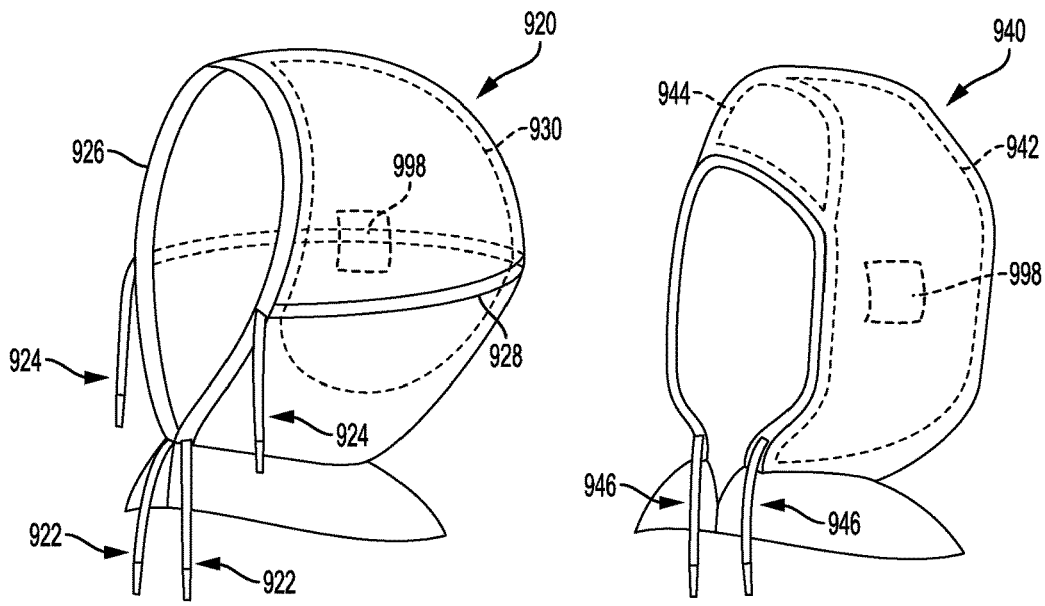
FIGS. 36-37 show examples hoods that incorporate a head guard.

As shown in FIG. 36, in some embodiments, a plurality of tightening or adjustment features can be used. The hood 920 in FIG. 36 comprises a padding layer 930. A first set of drawstrings 922 are positioned within a first hem 926 of the hood 920 and a second set of drawstrings 924 are positioned within a second hem 928 of the hood 920. By selectively drawing the first and/or second set of drawstrings 922, 924, the hood 920 can be tightened around the head of a wearer. As is to be appreciated, other forms of tightening features can be utilized, such as hook-and-loop fasteners, elastic members, cord locks, and so forth.

FIG. 37 illustrates yet another embodiment of a hood 940 incorporating a padded feature. The hood 940 comprises a first padding layer 942 and a second padding layer 944. The second padding layer 944 is positioned so that it is generally proximate the wearer's forehead. Drawstrings 946 can be selectively drawn to tighten the hood 940 around a wearer's head. The padding layers 904, 930, 942, and 944 can be any suitable type of material, such as, without limitation, one or more of the materials described above with reference to padding layer 340. The hoods 902, 920, and 940 are each schematically shown to include a sensory input and communications system 998.

Figure 38:
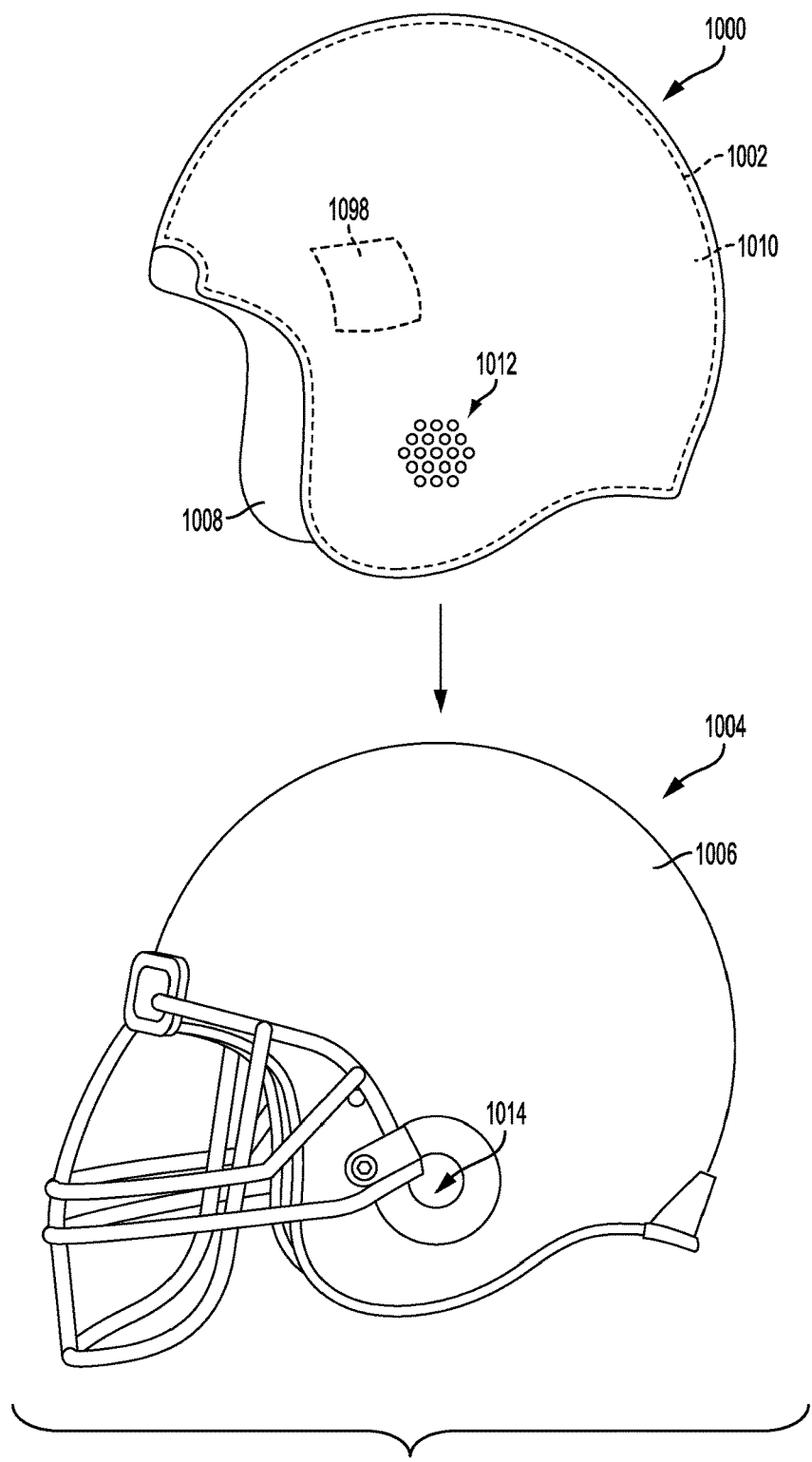
FIG. 38 shows a head guard for placement on the outside of an example helmet.

In some embodiments, head guards in accordance with the system and methods described herein can be worn by an athlete external to a helmet. An example head guard that can be worn on the outside of a helmet is illustrated in FIG. 38. The head guard 1000 can be compressive, or stretchable, such that it can be placed snugly around an outside surface 1006 of a football helmet 1004. In some configurations, the position of the head guard 1000 can be maintained through the compressive characteristics of the head guard 1000. In other embodiments, additional techniques can be utilized to attach the head guard to the helmet, such as adhesives, straps, buckles, hook-and-loop fasteners, and so forth. In any event, the head guard 1000 can comprise a padding layer 1002, similar to the other padding layers described herein. The head guard 1000 can comprise an inner surface 1008 that is generally slip-resistant that can aid in maintaining the proper positioning of the head guard 1000, even during an impact event. The head guard 1000 can comprise an outer surface 1010 that is a material that has a relatively low coefficient of friction that can allow the head guard 1000 (and underlying helmet) to generally slide across an object during impact, such as another football player. Example materials for outer surface 1010 include, without limitation, a polyester and nylon combinations include spandex or elastane. The head guard 1000 can also comprise ports 1012 that are positioned to generally align with the helmet port 1014 when the head guard 1000 is placed over the helmet 1004. The ports 1012 can be configured to generally allow sound to travel through the head guard 1000 so that the athlete's hearing is not affected when the head guard 1000 is positioned on the helmet 1004. As is to be appreciated, the particular design of the ports 1012 can vary in various embodiments. For example, in one embodiment the ports 1012 can comprise a single large port, while in another embodiment the port 1012 can comprise a series of slots. The head guard 1000 is also schematically shown to include a sensory input and communications system 1098.

Figure 39:
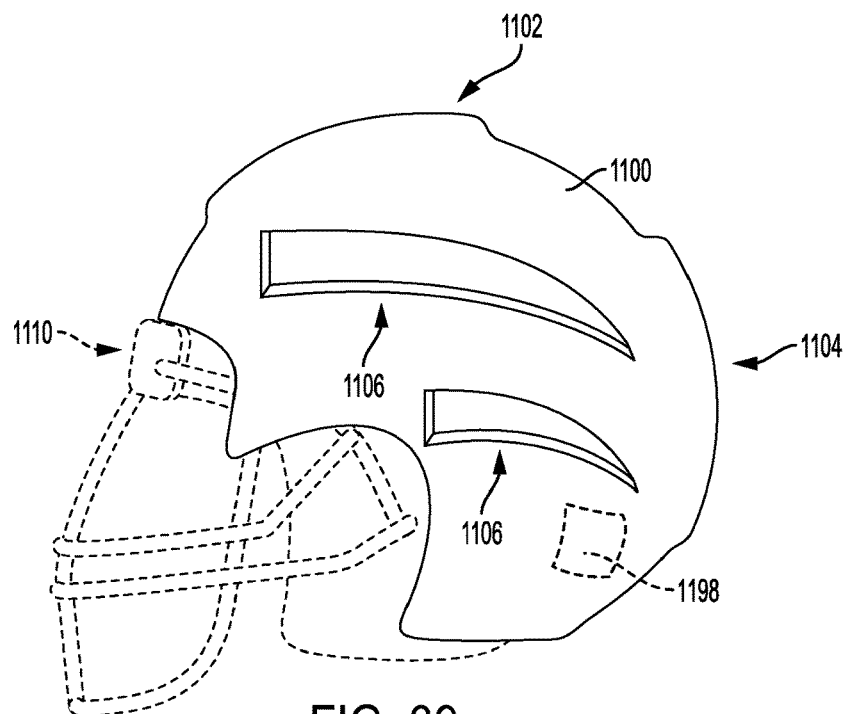
FIG. 39 shows an example head guard positioned on an example helmet.
Figure 40:
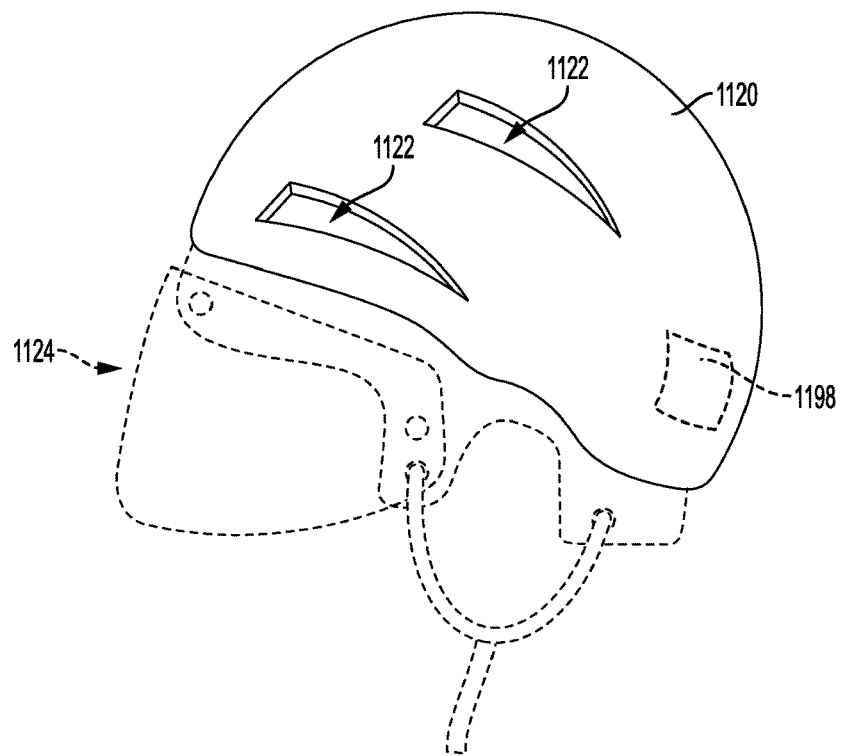
FIG. 40 shows another example head guard positioned on an example helmet.

FIGS. 39-40 show example head guards used in combination with various types of sporting helmets each of which is schematically shown to include a sensory input and communications system 1198. FIG. 39 shows a head guard 1100 coupled to a football helmet 1110. The head guard 1100 can be selectively removable from the helmet 1110 and be manufactured in different sizes to accommodate different helmet sizes. The outer surface of the head guard 1100 can be clear, a solid color, or a combination of colors. The outer surface can also include numbering, letters, words, graphics, and so forth. The head guard 1100 can also comprise one or more padded ridges or other areas of increased padding. In the illustrated embodiment, the head guard 1100 comprises a top ridge 1102, a rear ridge 1104, and side ridges 1106. These ridges can be unitary, or otherwise integral, with the head guard 1100 and can be manufactured from any suitable materials, such as foam, impact gel, Styrofoam, or any other suitable impact absorbing or dissipating materials. It is to be appreciated, that the head guards disclosed herein can be used or configured to be worn on the outside of a variety of helmet types. FIG. 40, for example, shows a head guard 1120 positioned over top of a hockey helmet 1124. The head guard 1120 comprises vents 1122 that can align with vents in the hockey helmet 1124. In some embodiments, the head guard 1120 can also include padded ridges, or other areas of increased thickness or density.

Figure 41:
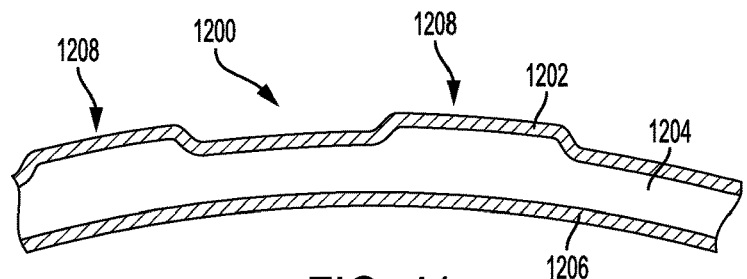
FIG. 41 shows a cross-sectional view of a head guard in accordance with one non-limiting embodiment.

FIG. 41 shows an example cross-sectional view of a head guard 1200 that can be positioned on the outside of a sporting helmet. The head guard 1200 comprises three layers, including an outer layer 1202, a padding layer 1204, and an inner layer 1206. In some embodiments, fewer or additional layers can be used. In the illustrated embodiment, the head guard 1200 also comprises ridges 1208. As discussed above, the inner layer 1206 can have a relatively high coefficient of friction, such that it has a tendency to adhere to or grip the outside surface of an associated helmet. The padding layer 1202 can comprise any suitable materials, including the variety of materials described above. The outer layer 1202 can have a relatively low coefficient of friction as compared to the inner layer 1206. Depending on the associated sporting event, the outer layer 1202 may be in contact with various objects, such as other player's jerseys, helmets, and so forth. With the outer layer 1202 having a relatively low coefficient of friction, during those impact events, the head guard 1200 can behave similarly to the outer surface 1006 (FIG. 36) of the underlying helmet. The head guard 1200 (with or without the ridges 1208) can be used in combination with a wide variety of helmet types, including, without limitation, baseball, hockey, bicycling, and skateboarding, for example.

Figure 42:
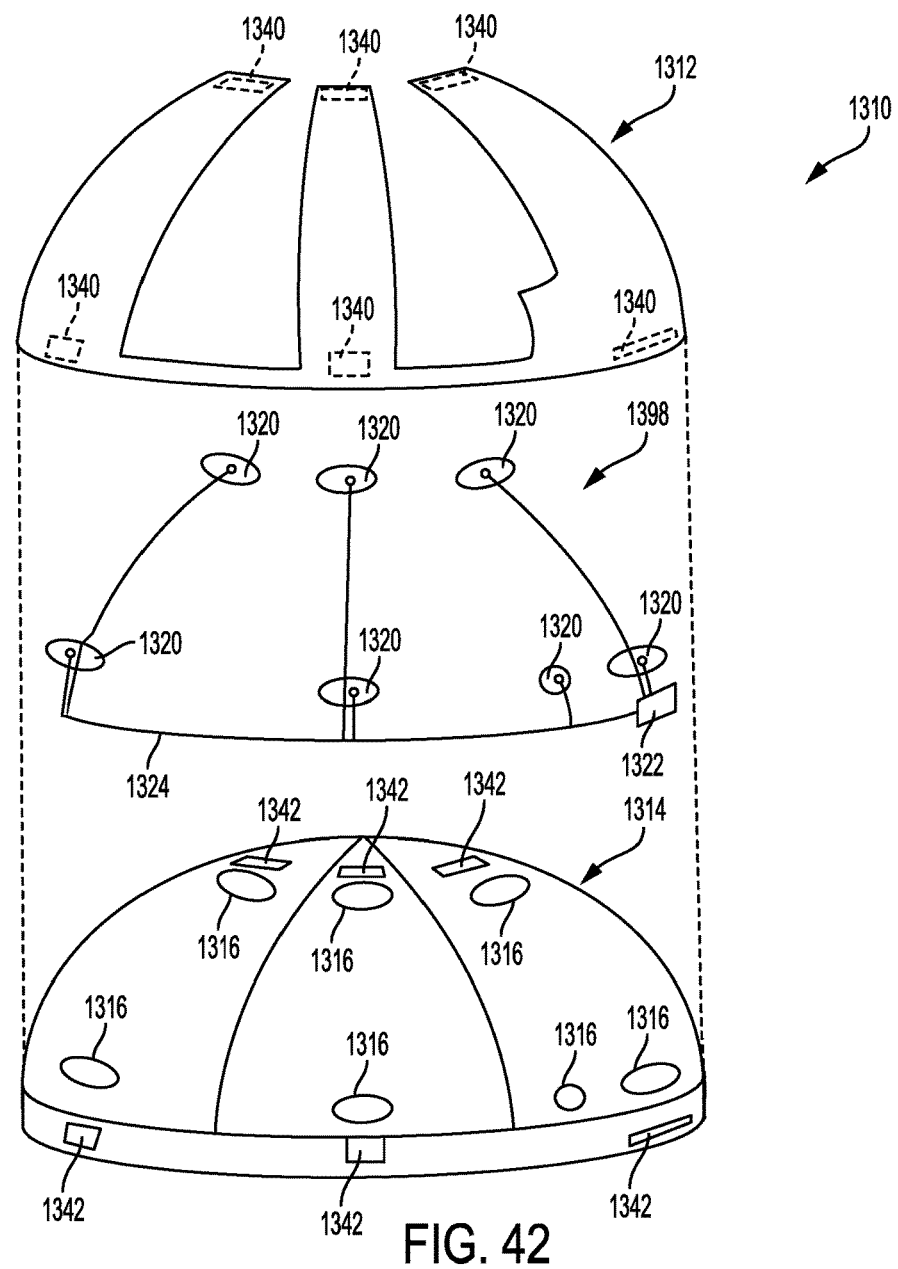
FIG. 42 is an exploded view of a head guard in accordance with one non-limiting embodiment.
Figure 43:
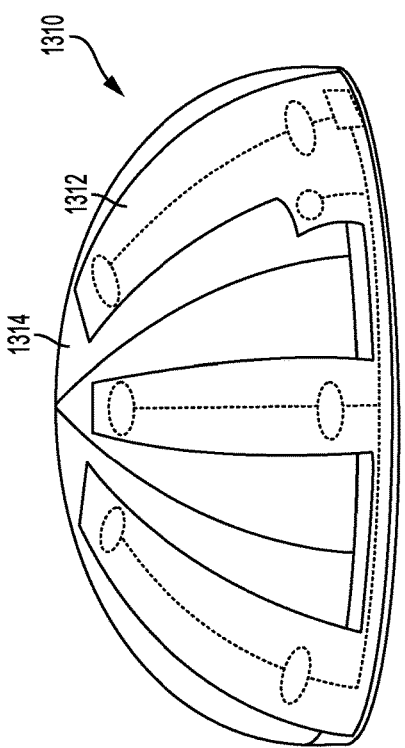
FIG. 43 depicts the head guard FIG. 42 fully assembled.

FIG. 42 is an exploded view of a head guard 1310 in accordance with one non-limiting embodiment. FIG. 43 depicts the head guard 1310 of FIG. 42 fully assembled. The head guard 1310 can have a cover system 1312 that can be selectively attached to a base unit 1314. The cover system 1312 can be selectively attachable to the base unit 1314 such that some or all of a sensory input and communications system 1398 can be accessed, and in some cases, removed. In the illustrated example, the sensory input and communications system 1398 is depicted as including a plurality of sensors 1320. The sensors 1320 can be any suitable sensor type, as described in more detail below. The sensors 1320 can be in communication with a microcontroller 1322 via a sensor bus 1324. In some embodiments, one or more sensors 1320 can communicate with the microcontroller 1322 via wireless communication. The base unit 1314 can define a plurality of bores, recesses, connectors, clips, pads, or other receiving units (schematically shown as sensor ports 1316). In the illustrated embodiments, at least some of the sensory input and communications system 1398 can be inserted into the sensor ports 1316 and the cover system 1312 attached to the base unit 1314 (as shown in FIG. 43). In the illustrated embodiment, fasteners 1340 on the cover system 1312 are configured to attach to fasteners 1342 on the base unit 1314. Examples of fasteners 1340 and 1342 can include, without limitation, hook and loop fasteners, magnetic fasteners, snaps, buttons, and clasps. In some embodiments, some or all the sensory input and communications system 1398 can be separated from the base unit 1314 and the cover system 1322 so that they can be washed or sterilized, for example. Additionally, different sensory input and communications systems 1398 can be connected to the head guard 1310, such as to provide different sensors arrays, for example. Furthermore, while FIGS. 42-43 generally depict a domed-shaped head guard, it is to be readily appreciated that a similar cover system can be used with head guards having different form factors (i.e., headband configurations) without departing from the scope of the present disclosure.

Figure 44A:
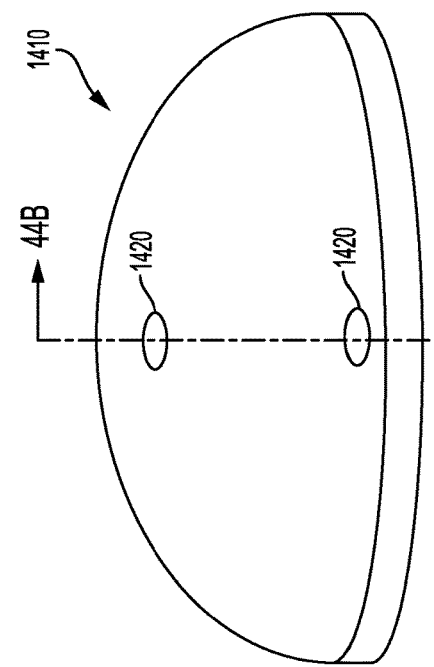
FIG. 44A shows a side view of an example head guard that includes sensors in accordance with one non-limiting embodiment.
Figure 44B:
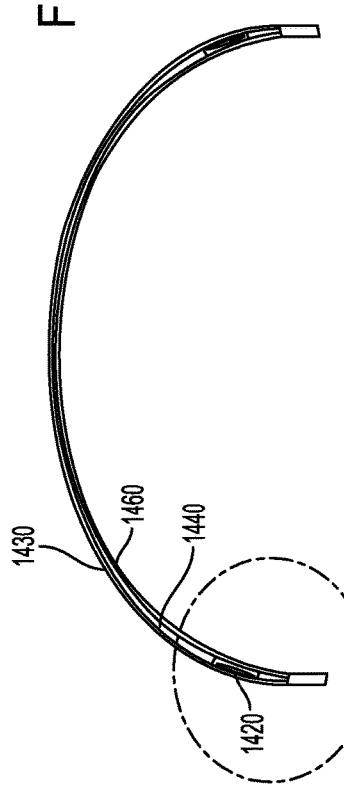
FIG. 44B shows a cross-sectional view of FIG. 44A taken alone line 44B-44B.
Figure 44F:
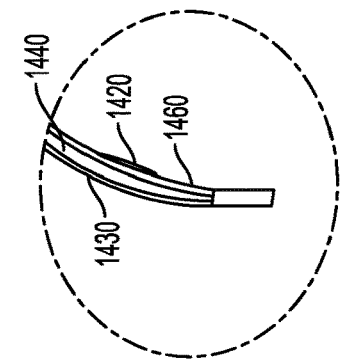
FIGS. 44C-44F each depict an enlarged section of FIG. 44B.
Figure 44E:
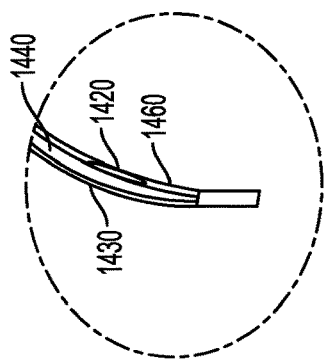
Figure 44D:
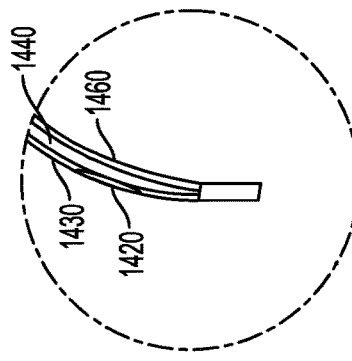
Figure 44C:
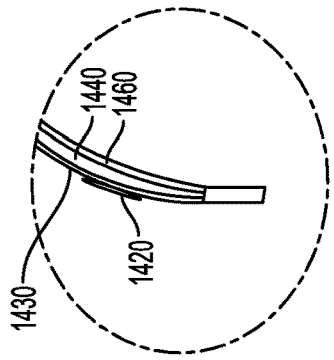

FIG. 44A shows a side view of an example head guard 1410 that includes sensors 1420. The sensors 1420 can be a component of a sensory input and communications system, as described herein. FIG. 44B shows a cross-sectional view of FIG. 44A taking along line 44B-44B. Similar to FIG. 17B, for example, the head guard 1410 is shown having an inner layer 1460, an outer layer 1430 and a padding layer 1440. In this embodiment, the sensors 1420 are placed between the inner layer 1460 and the outer layer 1430. In other embodiments, however, the placement location can vary. FIG. 44C depicts a sensor 1420 attached to the outer surface of the outer layer 1430. FIG. 44D depicts a sensor 1420 integral with (e.g., embedded) into the outer layer 1430. FIG. 44E depicts a sensor 1420 integral with (e.g., embedded) into the inner layer 1460. FIG. 44F depicts a sensor 1420 attached to the inner surface of the inner layer 1460.

Figure 45:
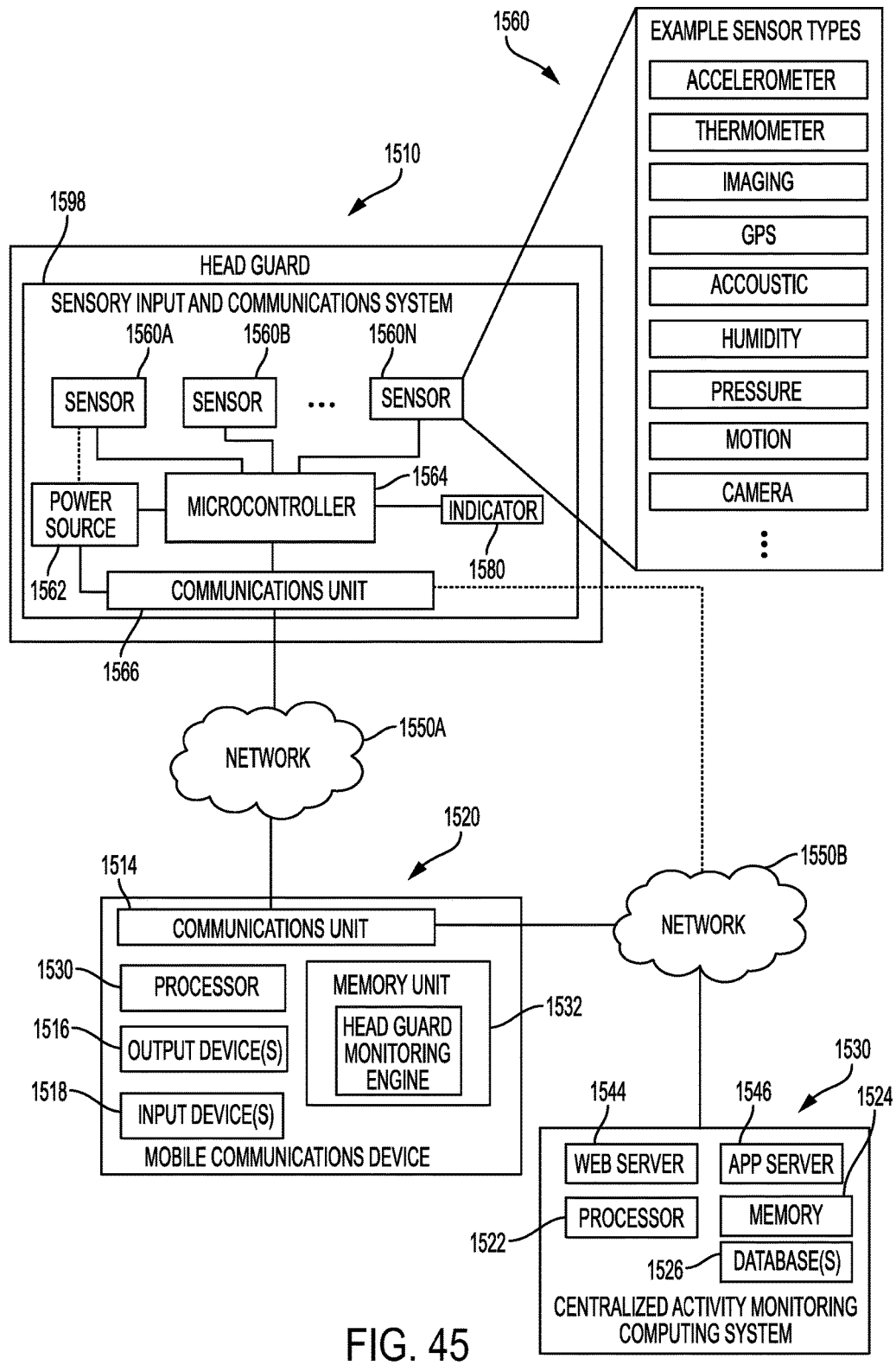
FIG. 45 depicts an example system diagram comprising a head guard in communication with a mobile communication device via one or more communications networks in accordance with one non-limiting embodiment.

Referring now to FIG. 45, which depicts an example system diagram comprising a head guard 1510 in communication with a mobile communication device 1520 via one or more communications networks 1550A. In some embodiments, the head guard 1510 and/or the mobile communication device 1520 can be in communication with a centralized activity monitoring computing system 1530 via one or more communications networks 1550B. The centralized activity monitoring computing system 1530 can be provided using any suitable processor-based device or system, such as a personal computer, laptop, server, mainframe, other processor-based device, or a collection (e.g. network) of multiple computers, for example. In some embodiments, the centralized activity monitoring computing system 1530 can generally be a cloud-based service available to a plurality of users through various communication networks.

The centralized activity monitoring computing system 1530 can include one or more processors and one or more memory units. For convenience, only one processor 1522 and only one memory unit 1524 are shown in FIG. 45. The processor 1522 can execute software instructions stored on the memory unit 1524. The processor 1522 can be implemented as an integrated circuit (IC) having one or multiple cores. The memory unit 1524 can include volatile and/or non-volatile memory units. Volatile memory units can include random access memory (RAM), for example. Non-volatile memory units can include read-only memory (ROM) as well as mechanical non-volatile memory systems, such as a hard drive, optical disk drive, or other non-volatile memory. The RAM and/or ROM memory units can be implemented as discrete memory ICs.

When the processor 1522 of the centralized activity monitoring computing system 1530 executes the software instructions of the memory unit 1524, the processor 1522 can be caused to perform the various operations of the centralized activity monitoring computing system 1530. The various operations of the centralized activity monitoring computing system 1530 can include, but are not limited to, the following: create and maintain user accounts; receive activity data from one or more head guards; receive activity data from one or more mobile communication devices; data analytics; reporting; trend analysis; visualize data; as well as perform other operations as discussed in more detail below.

The activity monitoring computing system 1530 can use data from various sources, including, but not limited to, one or more databases 1526. The data stored in the databases 1526 can be stored in a non-volatile computer memory, such as a hard disk drive, read only memory (e.g. a ROM IC), or other types of non-volatile memory. In some embodiments, one or more of the databases 1526 can be stored on a remote electronic computer system and can be accessed by the activity monitoring computing system 1530 via the communications network 1550B. As one having ordinary skill in the art would appreciate, a variety of other databases or other types of memory storage structures can be utilized or otherwise associated with the activity monitoring computing system 1530.

Also shown in FIG. 45, the activity monitoring computing system 1530 can include one or more computer servers, which can include one or more web servers, one or more application servers, and/or one or more other types of servers. For convenience, only one web server 1544 and one application server 1546 are depicted in FIG. 45, although one having ordinary skill in the art would appreciate that the disclosure is not so limited. The servers 1544, 1546 can allow content to be sent or received from one or more mobile communication devices 1520, as described in more detail below, via the communication network 1550B in any of a number of formats, which can include, but are not limited to, text-based messages, multimedia messages, email messages, smart phone notifications, web pages, and other message formats. The servers 1544, 1530 can be comprised of processors (e.g. CPUs), memory units (e.g. RAM, ROM), non-volatile storage systems (e.g. hard disk drive systems), and other elements. The servers 1544, 1546 may utilize one or more operating systems including, but not limited to, Solaris, Linux, Windows Server, or other server operating systems.

In some embodiments, the web server 1544 can provide a graphical web user interface through which various users can interact with the activity monitoring computing system 1530. The graphical web user interface can also be referred to as a graphical user interface, client portal, client interface, graphical client interface, and so forth. The web server 1544 can accept requests, such as HTTP requests, from various entities, including but not limited to first entities, second entities, and third entities, and serve responses to those entities, such as HTTP responses, along with optional data content, such as web pages (e.g. HTML documents) and linked objects (such as images, video, and so forth). The application server 1546 can provide a user interface for users who do not communicate with the activity monitoring computing system 1530 using a web browser. Such users can have special software installed on their communication devices 1520 to allow the user to communicate with the application server 1546 via the communication network 1550B.

The activity monitoring computing system 1530 can be in communication with a plurality of mobile communication devices via the communications network 1550B. For convenience, only one mobile communication device 1520 is schematically depicted in FIG. 45. The network 1550B can be an electronic communications network and can include, but is not limited to, the Internet, LANs, WANs, GPRS networks, other networks, or combinations thereof. The network 1550B can include wired, wireless, fiber optic, other connections, or combinations thereof. In general, the communications network 1550B can be any combination of connections and protocols that will support communications between the activity monitoring computing system 1530 and the mobile communication device 1520, As shown by the exemplary embodiment in FIG. 45, a head guard 1510 can be associated with (e.g., electronically linked in a wireless communication arrangement) a mobile communication device 1520. The mobile communication device 1520 can be any type of computer device suitable for communication over a network. The mobile communication device 1520 can be any of, for example, a laptop computer (which also includes a netbook or other portable computing device), a desktop computer, a tablet computer, a personal digital assistant (PDA), a smartphone (combination telephone and handheld computer), or other suitable mobile communications device (such as a networked gaming device, a media player, for example). In some embodiments, the mobile communication device 1520 can be a wearable computing device. Examples of wearable computing devices include devices that incorporate an augmented reality head-mounted display as well as other computing devices that can be worn on the body of the user, such as worn on the wrist.

In some embodiments, a user of the mobile communication device 1520 (such as a parent, athlete, coach, trainer, etc.) can install special software on the mobile communication device 1520 to allow the user to communicate with the application server 1546 via the communication network 1550B. The software for the mobile communication device 1520 can be downloaded to the communication device via the communication network 1550B or installed through other techniques known in the art. In some embodiments, the software may be downloaded from the activity monitoring computing system 1530. In some embodiments, the software can be an app that is available from the Apple™ iStore™, or another app store, for downloading onto and executing on an Apple™, iPhone™, or iPad™.

In some embodiments, the mobile communication device 1520 can provide a variety of applications for allowing the user to accomplish one or more specific tasks. Applications can include, for example, a web browser application (e.g. INTERNET EXPLORER, MOZILLA, FIREFOX, SAFARI, OPERA, GOOGLE CHROME, and others), telephone application (e.g. cellular, VoIP, PTT, or other), networking application, messaging application (e.g. e-mail, IM, SMS, MMS, BLACKBERRY Messenger, and others), and so forth. The mobile communication device 1520 can include various software programs such as system programs and applications to provide computing capabilities in accordance with the described embodiments. System programs can include, but are not limited to, an operating system (OS), device drivers, programming tools, utility programs, software libraries, application programming interfaces (APIs), and so forth. Exemplary operating systems can include, for example, a PALM OS, MICROSOFT WINDOWS, OS X, iOS, ANDROID OS, UNIX OS, LINUX OS, SYMBIAN OS, EMBEDIX OS, Binary Runtime Environment for Wireless (BREW) OS, Java OS, a Wireless Application Protocol (WAP) OS, and others. The mobile communication device 1520 can also include one or more communications units 1514 for communicating data using various network protocols. For example, the mobile communications device 1520 can be electronically linked to the head guard 1510 through a BLUETOOTH linkage, or other near filed communication (NFC) protocol, using the communications network 1550A for contactless data transmission. Such data transmission can occur in substantially real-time if the head guard 1510 is within range of the mobile communication device 1520. In some embodiments, the head guard 1510 can locally collect data and once wireless communication is established with the mobile communication device 1520, the head guard 1510 can transmit the collected data. Furthermore, in some cases, certain types of high priority data are provided by the head guard 1510 in substantially real-time, while other types of lower priority data are provided by the head guard 1510 subsequent to data collection.

The mobile communication device 1520 can include various components for interacting with the head guard 1510 and/or the activity monitoring computing system 1530, such as a display or a keypad/keyboard for inputting data and/or commands. The mobile communication device 1520 can include other components for use with one or more applications such as a stylus, a touch-sensitive screen, keys (e.g. input keys, present and programmable hot keys), buttons (e.g. action buttons, a multi-directional navigations button, preset and programmable shortcut buttons), switches, a microphone, camera, speakers, an audio headset, and so forth. Such components are schematically depicts as output devices 1516 and input devices 1518. The mobile communications device 1520 can also include one or more processors and one or more memory units. For convenience, only one processor 1522 and only one memory unit 1532 are shown in FIG. 45. The processor 1522 can execute software instructions stored on the memory unit 1524. The memory unit 1525 can store instructions for a head guard monitoring engine 1532, as described in more detail below.

The head guard 1510 can be any suitable style, design, or configuration of head guard, such as, without limitation, any of the head guards depicted in FIGS. 1-41, above. The head guard 1510 can include a sensory input and communications system 1598, as schematically depicted in FIG. 45. The sensory input and communications system 1598 can include, for example, sensors 1560 (schematically shown as 1560A, 1560B . . . 1560N). The particular type of sensors 1560 and the particular number of sensors 1560 used for a particular head guard can vary. In some embodiments, example sensor types include, but are not limited to, accelerometer sensors, thermometers, imaging sensors, GPS sensors, acoustic sensors, humidity sensors, pressure sensors, motion sensors, cameras, and others. The sensors 1560, or portions thereof, can be rigid or flexible. The sensors 1560 can assist with collecting data associated with any of the following: hit count (number of hits), impact location, impact duration, impact direction, impact reduced by impact absorption technology, and so forth. Some or all of the sensors can be low-profile. In some embodiments, the sensors 1560, or portions thereof, are encapsulated, sealed, or otherwise coated to provide water resistance or to make the sensors water proof. Such encapsulation can also aid in impact resistance and increase durability. In some embodiments, pockets or portions of the head guard 1510 receiving the sensors 1560 are sealed or sealable to prevent moisture penetration. Various sensors 1560 can be coupled (either permanently or temporarily) to the head guard 1510 using any suitable technique. The sensor 1560 can be individual sensors or multi-metric sensor capable of providing multiple metrics from a single component. The sensory input and communications system 1598 can execute diagnostic routines to confirm the operability of the various sensors 1560, with alerts generated with a potential issue is detected.

As illustrated, the head guard 1510 can include multiple sensors to assist with the collection of accurate data. Utilizing a plurality of sensors can facilitate impact validation and reconcile possible gaps in data collection. For instance, data received from one or more accelerometer sensors can be reconciled with data received from one or other sensor types. Based on multiple data points and information collected from different sensing capabilities, the software will be able to formulate an animated 3D visual of the exact area of the hit in the head.

In some embodiments, one or more temperature sensors, or other data sources can be utilized to monitor or otherwise receive information regarding the ambient temperature, precipitation, and/or other weather conditions in which the wearer of the head guard 1510 is experiencing. For instance, one or more sensors 1560 of the head guard 1510 can sense the ambient temperature information and provide such information to the mobile communications device 1520, either for local processing or for delivery to the activity monitoring computing system 1530. Additionally or alternatively, the mobile communications device 1520 can utilize a weather software application executing on the mobile communications device 1520, or other technique for data retrieval (i.e., API calls to a weather data feed) to receive the current temperature and/or other atmospheric conditions (precipitation, visibility, wind, etc.). Furthermore, the activity monitoring computing system 1530 can ascertain the weather conditions associated with the head guard 1510, such as through obtaining weather conditions for the geographic location in which the head guard 1510 is being used based on GPS coordinates, or otherwise. For instance, the head guard 1510 can be registered to a player in a particular geographic region so the activity monitoring computing system 1530 can poll a weather data source for weather-related data for that geographic region. The weather condition data can be used by the mobile communications device 1520 and/or the activity monitoring computing system 1530 for any suitable processing function. For instance, the weather condition data can be used as additional input for assessing effect of impacts or other types of monitored events, especially if certain types of injuries may be more prevalent in certain weather conditions. This data can be used, for example, to examine or determine potential correlations between monitored events and weather conditions, weather patterns, or other weather-related information that the wearer was experiencing at the time of the monitored event (i.e., heat exhaustion, injury, or otherwise).

The sensory input and communications system 1598 can also include a power source 1562, which can be, for example, a battery, a solar-energy source, any other suitable power supply. The power source 1562 can also leverage power harvesting techniques such as body heat, solar power, kinetic energy derived from sports activities, etc. to generate power to operate the sensory input and communications system 1598. In some embodiments, the power source 1562 can be wirelessly rechargeable, with electromagnetic fields of a charging unit transferring power from the charging unit to the power source 1562.

The sensory input and communications system 1598 can also include a microcontroller 1564 for receiving outputs from the sensors 1560A, 1560B . . . 1560B. The microcontroller 1564 can be in communication with a communication unit 1566, which can be, for example, a BLUETOOTH communications module. The communication unit 1566 can include any type of transmitter, transceiver, and/or antenna to enable suitable communication. In some embodiments the communication unit 1566 can operate utilizing one or more communication protocols, such as LTE, Wi-Fi, radio frequency, and so forth. In some cases, signal strength and data traffic is considered to determine which communication to use during a particular sporting event. The antenna(s) of the communication unit 156 can be multi-band to support one or more of following frequencies: Bluetooth wireless technology: 400 MHZ: 400-450, 600 MHz: 608-614, 900 MHZ: 950-956, ZigBee 902-928 MHZ, ZigBee: 2400-2483.5 MHZ, UWB: 3168-10560 MHZ, NFC: 13.56 MHZ, Global Navigation Satellite Systems: GPS 1565-1585 MHZ, DVB-H: 1670-1675 MHz, WiMax: 2300-3800 MHz, GSM/UMTS: 850-2170 MHZ single and multi-band, LTE: 700-3700 MHZ multi band, 4900-5875 MHZ. Furthermore, various components of the communication unit 1566, such as an antenna, can be made through laser direct structuring, molded interconnected devices, and other technologies for 3D antenna. The antenna can also be an energy harvesting antenna that converts various electromagnetic fields to energy that can be utilized by the power source 1562. In some embodiments, the sensors 1560A, 1560B . . . 1560N themselves can communicate directly with the mobile communications device 1520. Furthermore, a variety of communication techniques can be used, such as 900 MHz wireless transmissions.

The sensory input and communications system 1598 can also include a local indicator 1580 that provides one or more indications when certain events are detected. For instance, local indicator 1580 can be a visual and/or audio device that is activated by the microcontroller 1564 when an impact event of a predefined magnitude is detected. Such local indicator 1580 can therefore provide the wearer, a referee, or other observer an indication that a certain type of event has been detected. In some embodiments, the output of the local indicator 1580 can vary depending on impact, or other factors. For instance, an impact at a first level may cause the local indicator 1580 to illuminate yellow and/or flash slowly while a much greater impact may cause the local indicator 1580 to illuminate red and/or quickly, and so forth. The output of the local indicator 1580 can be specific or customized to the athlete such that specific thresholds for impact, per sport, per age group, per gender can be implemented.

Further, while the local indicator 1580 is depicted as being in communication with the microcontroller 1564, this disclosure is not so limited. In some embodiments, alternative to a microcontroller-controlled local indicator or in addition to a microcontroller-controlled local indicator, the local indicator 1580 of the head guard 1510 can be a non-powered indicator that provides real-time impact visualization. For instance, the local indicator 1580 can be a color changing gel that changes color with impact (through heat); as heat is generated byproduct of an impact. The severity or level of impact can generate different colors to indicate impact severity (Green/Yellow/Red). Example gels include thermochromic gels, and other color changing gels that are impact activated. The gels can reset momentarily, returning to its original color and will activate again upon impact. This type of local indicator 1580 can be placed in front, side or back of the headgear and be viewable through a viewing port on the head guard 1510, for example.

Figure 46:
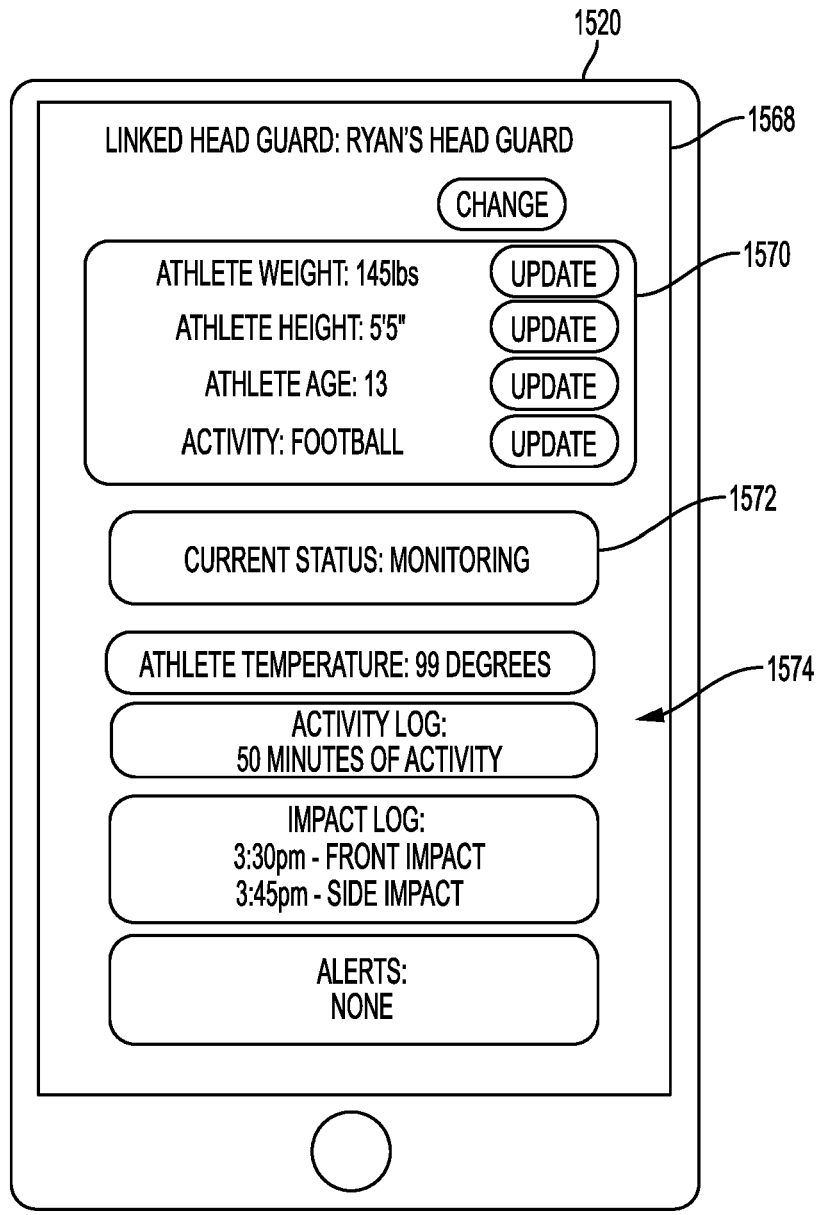
FIG. 46 depicts an example user interface that can be provided on a display of the mobile communications device depicted in FIG. 45.

FIG. 46 depicts an example user interface 1568 that can be provided on a display of the mobile communications device 1520 depicted in FIG. 45. Referring now to FIGS. 45-46, an exemplary non-limiting operational example will now be described. The head guard 1510 can be placed on the head of an athlete. The head guard 1510 can be linked to the mobile communications device 1520 through any suitable communications protocol using the network 1550A (such as a personal area network (PAN)). In some embodiments, a user of the mobile communications device 1520 can provide wearer data 1570, such as weight, height, age, activity, and so forth. Such data can be used to determine various performance/monitoring metrics, such as impact thresholds or ranges. Such metrics can be stored locally on the mobile communications device 1520 or retrieved from the centralized activity monitoring computing system 1530. In some embodiments, one or more algorithms can be used to determine the individual impact and temperature thresholds to determine risk levels for head trauma, and heat stroke, and other diagnostic based on captured or inputted athlete data (e.g., athlete's weight, age, height, and sport). The user interface 1568 can also indicate that the head guard is currently being monitored at status indicator 1572. Additional information 1574 can also be tracked and/or provided through the user interface 1568. The data can be information that was collected by one or more of the sensors 1560A, 1560B . . . 1560N, provided to the microcontroller 1564, and subsequently transmitted to the mobile communications device 1520. The data can be visualized by the user interface 1568, and in some cases, trends can be identified or determined. Such data can include, without limitation, duration of activity, distance traveled, temperature, brain activity, heart rate, respiration, impact events (location, magnitude), head rotation, sweat rate, images (still images, video), speed, and so forth. Visualization of the data can also include reconstruction of various impact events based on data collected from multiple sensors for one or more head guards involved with the event. For instance, 3-D modeling can be utilized to visually depict impact events for one or more head guards collecting data during the event. In some embodiments, if certain event thresholds are met, various alerts or notices can be provided to the user interface 1568 or sent to other recipient devices via other means (e.g., as email account, text messages, social media messages, instant messages). Such event thresholds can be based on, for example, impacts received, length of activity, temperature, distance traveled, and so forth. The alert or notice can be, for example, a graphical notice, an auditory notice, or combination of both.

Figure 47:
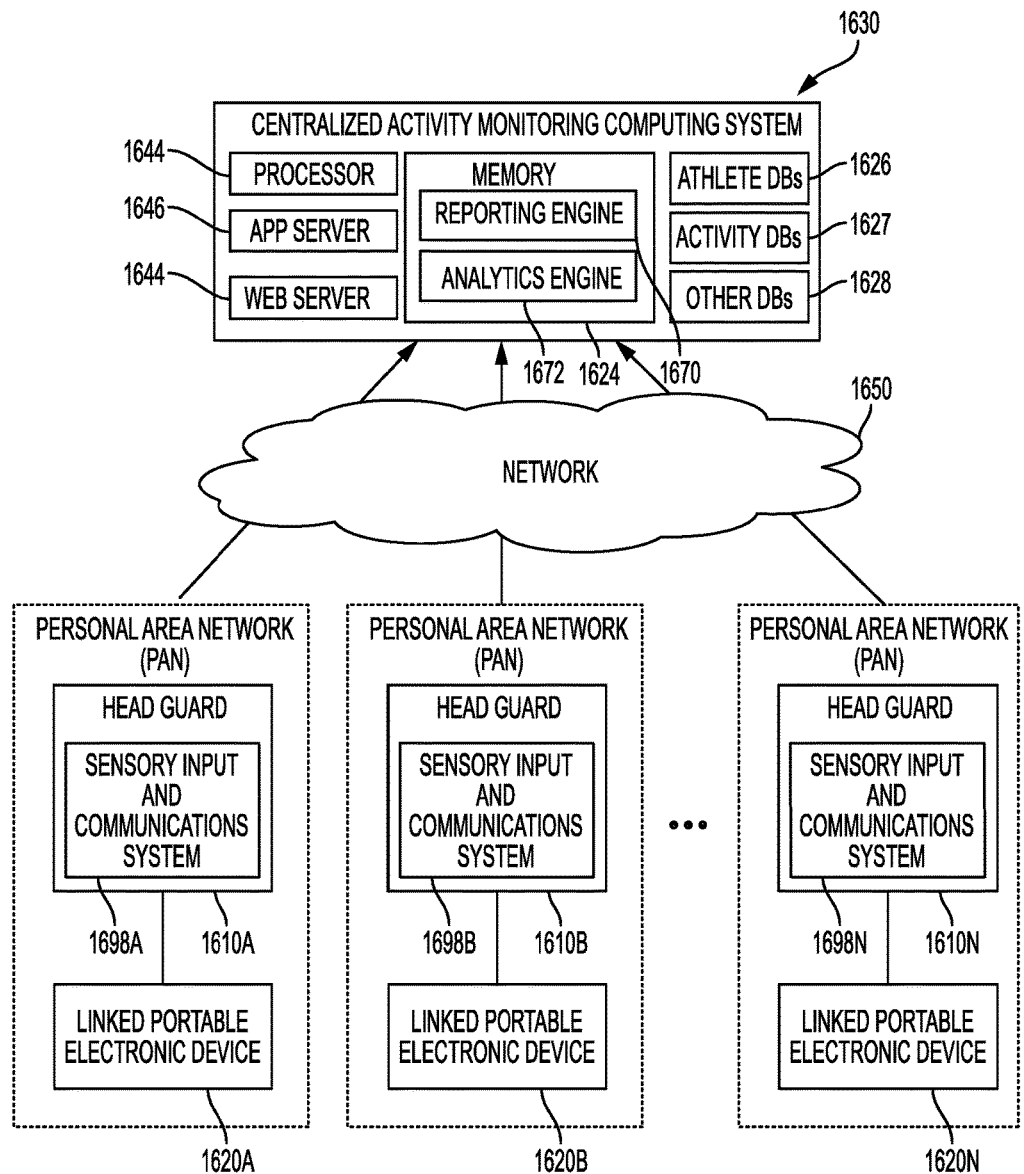
FIG. 47 depicts another system diagram of an example activity monitoring computing system in accordance with one non-limiting embodiment.

FIG. 47 depicts another system diagram of an example activity monitoring computing system 1630. The activity monitoring computing system 1630 can be in direct or indirect communication with a plurality of head guards 1610A, 1610B . . . 1610N through a communication network 1650. Each of the head guards 1610A, 1610B . . . 1610N can be electronically linked, such as through a personal area network (PAN), to a respectively linked portable electronic device 1620A, 1620B . . . 1620N. In one embodiment, each of the linked portable electronic devices 1620A, 1620B . . . 1620N is configured to provide various information to the activity monitoring computing system 1630 for data collection and subsequent processing by the activity monitoring computing system 1630. Such data can be transmitted in real-time, substantially real time, periodically, or based on a request from the activity monitoring computing system 1630. In some embodiments, all of the data collected by the sensor input and communications systems 1698A, 1698B . . . 1698N of each of the head guards 1610A, 1610B . . . 1610C can be provided to the activity monitoring computing system 1630. In other embodiments, a subset of the collected data can be provided. The activity monitoring computing system 1630 can include, similar to FIG. 45, a processor 1644, an app server 1646, a web server 1644, and various databases 1626, 1627, 1628. The activity monitoring computing system 1630 can also include a memory unit 1624 that can store instructions for various engines, such as a reporting engine 1670 and an analytics engine 1672. The activity monitoring computing system 1630 can, for example, provide aggregate reporting based on data received from a plurality of head guards 1610A, 1610B . . . 1610N. While the aggregate reporting can vary, example types of reports can include impacts levels per sport for a particular age group, activity levels per age group in a particular geographic area, and so forth. Additionally, the activity monitoring computing system 1630 and/or the linked portable electronic device 1620A, 1620B . . . 1620N can track and store data for individual athletes or groups of athletes (e.g., teams).

Figure 48:
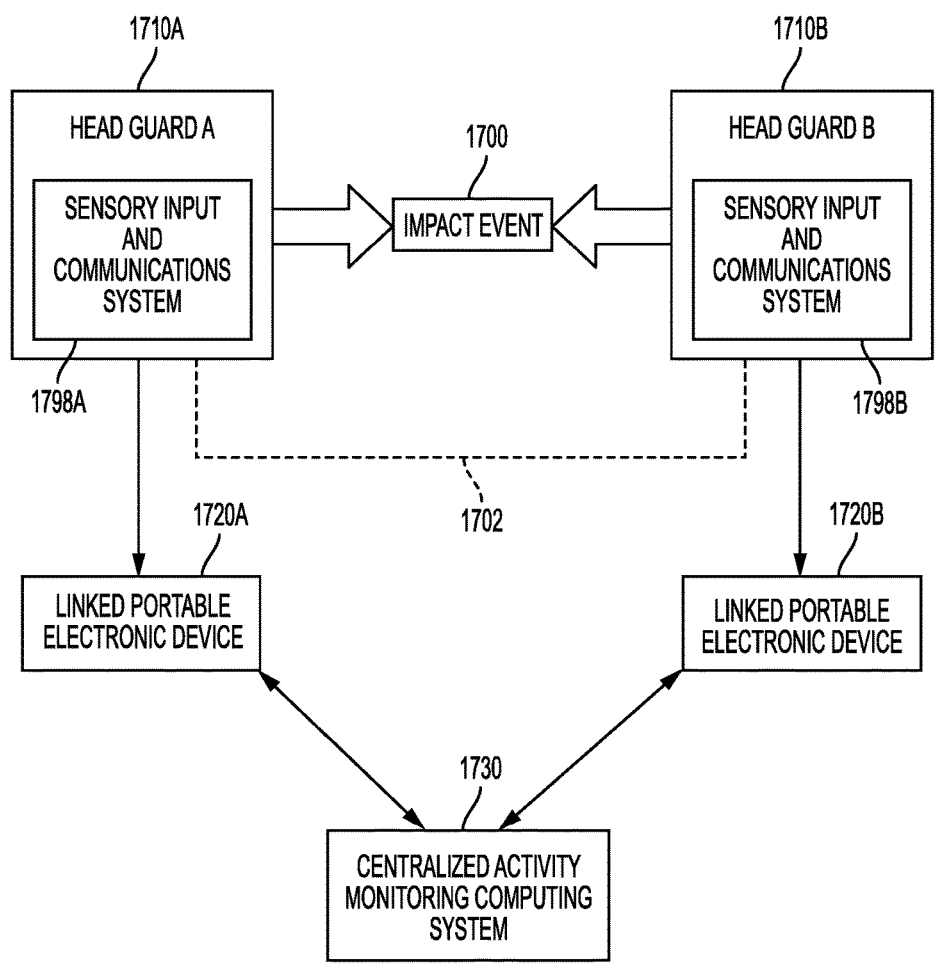
FIG. 48 schematically depicts a first head guard and a second head guard impacting during an athletic endeavor.

FIG. 48 schematically depicts a first head guard 1710A and a second head guard 1710B impacting during an athletic endeavor, with the impact being depicted as impact event 1700. While two head guards are depicted in FIG. 48, it is to be appreciated that various impact events 1700 can involve more than two head guards. As a result of the impact event 1700, sensors associated with a sensory input and communication system 1798A of the first head guard 1710A and sensors associated with a sensory input and communication system 1798B of the second head guard 1710B will generate various types of data. The data can be provided to the linked portable electronic devices 1720A and 1720B, respectively. In some embodiments, various data can also be exchanged between the first head guard 1710A and the second head guard 1710B via a datalink 1702. Using data received from each of the sensory input and communication systems 1798A and 1798B, an activity monitoring computing system 1730 can provide appropriate correlation of the hits in regards to other player. For example if two players collide head on, the impact to both players would be assessed from a variety of metrics including each of the players speed/acceleration before impact, based on the data collected by their respective head guards 1710A and 1710B. The profile of each player (i.e., height, weight, etc.) can also assist with creating a full picture of data collected during the impact event 1700. Thus, the activity monitoring computing system 1730 can track the impact received to the first head guard 1710A and detect that the athlete wearing the head guard 1710B delivered the impact. The wearer data (i.e. wearer data 570 shown in FIG. 46) of that athlete can be used by the activity monitoring computing system 1730 for processing.

Example data that can be tracked, stored, or otherwise processed by head guards in accordance with the present disclosure includes, without limitation, active minutes, top speed, impacts received, location of impacts, severity of impacts, average temperature, etc. Such data can be collected, gathered or presented over certain time frames, such as over a season, over a career, over a school year, over a tournament, over a game, and so forth. In some embodiments, the data collected can be reviewed and processed in the aggregate (e.g., using 'big data' approaches), and in other embodiments relatively small subsets of the data can be used for processing and review. In some embodiments, artificial intelligence, neural networks, or other types of learning networks can mine data collected from a plurality of head guards, as well as other sources, to extrapolate various information or datasets. In some embodiments, object tracking of the video data collected from the head guard (or from other source(s)) can be used in combination with data and metrics received from onboard sensors of one or more head guards. Using machine learning, or other computing platforms, various data regarding impact, acceleration/deceleration, mass, direction of individual and team players, and location of players can be correlated to various events (i.e., impact events) across a plurality of datasets.

Head guards in accordance with the presently disclosed embodiments may be manufactured using a variety of manufacturing techniques, such as ultrasonic welding, stitching, gluing, and/or quilting, for example. Stitching can be used to couple an interior fabric layer to an external fabric layer to create a pocket to house the padding layer. In some embodiments, double needle stitching is utilized to attach various components of the head guard. With a double stitching technique, twin needles create parallel double stitching using two needles mounted in a plastic holder. A standard needle shank is added to the plastic holder so it can be inserted in the needle holder on the sewing machine. One needle can be shorter than the other so that a bobbin can catch both stitches. The head guards can be manufactured in different sizes so that they can accommodate both children head sizes and adult head sizes.

The head guards disclosed herein can be used in a wide variety of endeavors, either as standalone units or in combination with existing protective gear, including both activities involving contact and non-contacting activities. Example applications include, without limitation, mixed martial arts, boxing, paintball, lacrosse, racquetball, water polo, ice skating, roller skating, water skiing, wind surfing, surfing, wrestling, rock climbing, ice hockey, roller hockey, basketball, soccer, wrestling masks, motocross, auto racing, cricket, BMX racing, parkour, and volleyball. Additional applications can include, without limitation, rodeo (for both riders and clowns), track & field events, cross-country running, hang gliding, bobsledding, and luge, for example. Other applications for the head guards described herein include, for example, skiing, snowboarding, skateboarding, rugby, polo, equestrian sports, martial arts, and base jumping. In some embodiments, the head guard may be worn as a component under the athlete's helmet. In some embodiments, the head guard may be incorporated into the athlete's apparel. In some embodiments, the head guard can be worn over top of a sporting helmet. In some embodiments, the head guard can be worn without a helmet.

When a head guard is worn under a helmet (such as a football helmet, hockey helmet, bicycle helmet, and the like), an impact delivered to the wearer's head may be reduced as compared to receiving the impact when wearing the rigid helmet without a head guard. When tested in general accordance with to the National Operating Committee of Standards for Athletic Equipment (NOCSAE) Documner (ND) 002-11m12, a head guard worn in combination with various types of football helmets can dissipate an impact force applied to the helmet as measured by severity index. For example, a severity index of an impact to a helmet can be higher than the severity index of the same impact delivered to the rigid helmet worn in combination with a head guard. Such impact dissipation can also occur when worn in combination with other helmets, such as lacrosse helmets, hockey helmets, and batting helmets in accordance with ND 041-11m12, ND 030-11m12, and ND 022-10m12, respectively. Such impact dissipation can also occur when worn in combination with other types of helmets, such as ski helmets, for example. As described herein, head guards in accordance with the present disclosure do not necessarily have to be worn in combination with a helmet. For such uses, an impact delivered to the wearer's head while wearing a head guard may be reduced as compared to receiving the impact when not wearing a head guard. Moreover, head guards in accordance with the present disclosure do not necessarily have to be worn with rigid helmets but can be worn in connection with baseball hats or other types of non-rigid hats. For such uses, an impact delivered to the wearer's head may be reduced as compared to receiving the impact when wearing the non-rigid hat without a head guard.

The particular combination of materials for the various layers of head guards manufactured in accordance with the systems and methods described herein can vary. Below are some non-limiting examples of material combinations. As is to be readily appreciated, other combinations are envisioned and are within the scope of the present disclosure. For some head guards, one or more layers can comprise about 80-90% polyester or Nylon and about 10-20% Spandex or Elastene. In one embodiment, one or more layers can comprise about 86% polyester and about 14% Spandex. One or more layers can also be a mesh-type material for increased breathability and ventilation. The layers of the head guard can have various fabric weights. In some embodiments, the fabric weight of an outer or inner lay can be in the range of about 5 to about 12 ounces, for example.

In some embodiments, one or more of the fabric layers can comprise about 60% polyester and about 40% cotton. In one embodiment, one or more fabric layers can comprise about 100% cotton. In one embodiment, one or more fabric layers can comprise about 80% polyester and about 20% spandex. In one embodiment, one or more fabric layers can comprise about 90% polyester and about 10% Spandex. In one embodiment, one or more fabric layers can comprise about 86% polyester and about 14% Spandex. In some embodiments, one or more fabric layers can comprise about 100% acrylic. In one embodiment, one or more layers can comprise about 85% acrylic and about 15% nylon.

In some embodiments, one or more fabric layers can comprise about 100% cotton. In one embodiment, one or more fabric layers can comprise about 80% cotton and about 20% polyester. Furthermore, various head guards can be manufactured from colored materials, dyed particular colors, or manufactured with glow in the dark and/or reflective materials.

In various embodiments disclosed herein, a single component may be replaced by multiple components and multiple components may be replaced by a single component to perform a given function or functions. Except where such substitution would not be operative, such substitution is within the intended scope of the embodiments. While various embodiments have been described herein, it should be apparent that various modifications, alterations, and adaptations to those embodiments may occur to persons skilled in the art with attainment of at least some of the advantages. The disclosed embodiments are therefore intended to include all such modifications, alterations, and adaptations without departing from the scope of the embodiments as set forth herein.

What is claimed is:

1. A data collection system, comprising
a head guard comprising:
   a multi-layered sidewall, wherein the multi-layered sidewall forms a dome, wherein the dome defines a circular opening for a head of a wearer and a plurality of sensor ports, and wherein the multi-layered sidewall comprises:
      a stretchable fabric layer, and
      a padding layer; and
   a removable cover system selectably attachable to the multi-layered sidewall, wherein the removable cover system has an inner surface and an outer surface, wherein a portion of the inner surface of the removable cover system is attachable to a portion of the dome to maintain the position of the removable cover system relative to the dome; and
   a sensory input and communications system, wherein at least a portion of the sensory input and communications system is positioned between the cover system and the multi-layered sidewall, the sensory input and communications systems comprises:
      a microcontroller,
      a plurality of sensors that are each in communication with the microcontroller, wherein each of the plurality of sensors are removably received into a respective one of the plurality of sensors ports,
      a communications unit, and
      a local indicator, wherein the microcontroller is configured to activate the local indicator upon a detected impact in excess of a predefined magnitude, wherein the local indicator comprises any of a visual device and an audio device; and
   an activity monitoring computing system to wirelessly receive data collected by the head guard, the activity monitoring computing system comprising at least one processor and non-transitory computer readable medium having instructions stored thereon which when executed by a processor cause the processor to:
      for the data received from the head guard, determine athlete information associated with the data based on the source of the data;
      group data based on one or more factors selected from the group of factors comprising sport, age, and geography; and
      generate aggregated data reporting based on the grouped data.

2. The data collection system of claim 1, comprising a plurality of head guards, wherein one of the plurality of head guards is a first head guard and another of the plurality of head guards is a second head guard, and wherein subsequent to an impact event between the first head guard and the second head guard detected by the activity monitoring computing system, the processor is to generate an impact report based on a first player associated with the first head guard and a second player associated with the second head guard.

3. The data collection system of claim 1, wherein the communications unit is configured to wirelessly transmit sensor data to an associated mobile communications device.

4. The data collection system of claim 3, wherein the activity monitoring computing system is to wirelessly receive sensor data from the associated mobile communications device.

5. The data collection system of claim 3, wherein the head guard is associated with the mobile communications device.

6. The data collection system of claim 1, wherein at least one of the plurality of sensors is attached to either or both of the stretchable fabric layer and the padding layer.

7. The data collection system of claim 1, wherein the plurality of sensors comprises one or more of an acceleration sensor, a heat sensor, and an impact sensor.

8. The data collection system of claim 1, wherein the communications unit is to transmit data collected by the sensor to a remote computing device.

9. The data collection system of claim 8, wherein the remote computing device is any of a mobile communications device, the activity monitoring computing system, and another head guard.

10. The data collection system of claim 8, wherein the data transmitted to the remote computing device comprises data collected during an impact event of the head guard.

11. The data collection system of claim 8, wherein the communications unit wirelessly transmits data to the remote computing device in substantially real-time.

12. The data collection system of claim 1, wherein the plurality of sensors are water resistant.

13. The data collection system of claim 1, wherein the communications unit comprises one or more antennas for data transmission over one or more of an long term evolution (LTE) network, a Wi-Fi network, a Bluetooth network, a ZigBee network, and a radio frequency network.

14. A data collection system, comprising
a plurality of head guards, wherein each of the plurality of head guards comprises:
    a multi-layered sidewall, wherein the multi-layered sidewall forms a dome, wherein the dome defines a circular opening for a head of a wearer and a plurality of sensor ports,
    a removable cover system selectably attachable to the multi-layered sidewall, and
    a sensory input and communications system, wherein at least a portion of the sensory input and communications system is positioned between the cover system and the multi-layered sidewall, the sensory input and communications systems comprises:
        a microcontroller,
        a plurality of sensors that are each in communication with the microcontroller, wherein each of the plurality of sensors are removably received into a respective one of the plurality of sensors ports,
        a communications unit, and
        a local indicator, wherein the microcontroller is configured to activate the local indicator upon a detected impact in excess of a predefined magnitude, wherein the local indicator comprises any of a visual device and an audio device; and
an activity monitoring computing system to wirelessly receive data collected by each of the plurality of head guards, the activity monitoring computing system comprising at least one processor and non-transitory computer readable medium having instructions stored thereon which when executed by a processor cause the processor to:
    generate aggregated data reporting based on the grouped data.

15. The data collection system of claim 14, wherein the plurality of head guards comprises a first head guard and a second head guard, and wherein subsequent to an impact event detected by the activity monitoring computing system, the processor is to generate an impact report.

16. The data collection system of claim 14, wherein each of the communications unit is configured to wirelessly transmit sensor data to an associated mobile communications device.

17. The data collection system of claim 16, wherein the activity monitoring computing system is to wirelessly receive sensor data from the associated mobile communications device.

18. The data collection system of claim 16, wherein the plurality of head guards are each associated with the mobile communications device.

19. A data collection system, comprising
a head guard comprising:
    a multi-layered sidewall, wherein the multi-layered sidewall defines a circular opening for a head of a wearer;
    a removable cover system selectably attachable to the multi-layered sidewall; and
    a sensory input and communications system, wherein the sensory input and communications systems comprises:
        a microcontroller,
        a plurality of sensors that are each in communication with the microcontroller, and
        a communications unit; and
an activity monitoring computing system to wirelessly receive data collected by the head guard, the activity monitoring computing system comprising at least one processor and non-transitory computer readable medium having instructions stored thereon which when executed by a processor cause the processor to:
    group data based on one or more factors selected from the group of factors comprising sport, age, and geography; and
    generate aggregated data reporting based on the grouped data.

20. The data collection system of claim 19, wherein the communications unit is configured to wirelessly transmit sensor data to an associated mobile communications device and wherein the activity monitoring computing system is to wirelessly receive sensor data from the associated mobile communications device.

* * * * *